United States Patent
Yang et al.

(10) Patent No.: US 8,450,674 B2
(45) Date of Patent: May 28, 2013

(54) ACOUSTIC ASSISTED PHASE CONJUGATE OPTICAL TOMOGRAPHY

(75) Inventors: Changhuei Yang, Pasadena, CA (US); Charles DiMarzio, Cambridge, MA (US); Meng Cui, Ashburn, VA (US); Ying Min Wang, Pasadena, CA (US)

(73) Assignees: California Institute of Technology, Pasadena, CA (US); Northeastern University, Boston, MA (US)

( * ) Notice: Subject to any disclaimer, the term of this patent is extended or adjusted under 35 U.S.C. 154(b) by 370 days.

(21) Appl. No.: 12/943,841

(22) Filed: Nov. 10, 2010

(65) Prior Publication Data

US 2011/0108707 A1   May 12, 2011

Related U.S. Application Data

(60) Provisional application No. 61/355,328, filed on Jun. 16, 2010, provisional application No. 61/259,975, filed on Nov. 10, 2009, provisional application No. 61/260,316, filed on Nov. 11, 2009, provisional application No. 61/376,202, filed on Aug. 23, 2010.

(51) Int. Cl.
    *H01L 27/00*   (2006.01)

(52) U.S. Cl.
    USPC .......... 250/208.1; 250/214.1; 250/493.1; 250/494.1; 378/4; 378/21; 378/901; 382/131

(58) Field of Classification Search
    USPC ............ 250/208.1, 458.1, 214.1, 214 R, 250/493.1, 494.1; 378/4, 21, 23, 24, 25, 26, 378/27, 901; 382/131
    See application file for complete search history.

(56) References Cited

U.S. PATENT DOCUMENTS

| | | | |
|---|---|---|---|
| 4,866,781 A | 9/1989 | Borken et al. | |
| 4,928,695 A | 5/1990 | Goldman et al. | |
| 4,945,239 A | 7/1990 | Wist et al. | |
| 5,760,388 A | 6/1998 | Swandic | |
| 6,707,020 B1* | 3/2004 | Praus et al. | 250/201.9 |
| 2012/0194814 A1* | 8/2012 | Wang | 356/301 |

OTHER PUBLICATIONS

International Search Report for International Application No. PCT/US2010/056270 filed on Nov. 10, 2010.
Poster: Xu et al.; "Time Reversal Ultrasound Optical Tomography Using a BSO Phase Conjugate Mirror". Optical Imaging Laboratory, Department of Biomedical Engineering, Washington University in Saint Louis; Jan. 2009.
Boas, D. et al., "Imaging the body with diffuse optical tomography," IEEE Signal Processing, vol. 18, pp. 57-75, 2001.

(Continued)

*Primary Examiner* — Francis M Legasse, Jr.
(74) *Attorney, Agent, or Firm* — Gates & Cooper LLP

(57) ABSTRACT

A light microscope for imaging a sample containing one or more fluorescent agents, comprising a source for generating acoustic waves that are focused at a focus in the sample, wherein the acoustic waves frequency shift a frequency of light passing through the focus, thereby creating a frequency shifted light beam; at least one spatial light modulator (SLM) positioned to illuminate the sample with an output beam that is an optical phase conjugate of the frequency shifted light beam, wherein the output beam is a reflection of a first reference beam off one or more pixels of the SLM, and the pixels are for modulating the first reference beam to create the output beam; and a detector positioned to detect fluorescence generated by the output beam exciting the fluorescent agents at the focus in the sample, thereby imaging the sample.

23 Claims, 8 Drawing Sheets

OTHER PUBLICATIONS

Campagnola, P. et al., "Second-harmonic imaging microscopy for visualizing biomolecular arrays in cells, tissues and organisms," Nature Biotechnology, vol. 21, No. 11, Nov. 2003, 1356.
Cui, M. et al., "An in vivo study of turbidity suppression by optical phase conjugation (TSOPC) on rabbit ear," Optics Express 18, No. 1, Jan. 4, 2010, 25.
Cui, M. et al., "Implementation of a digital optical phase conjugation system and its application to study the robustness of turbidity suppression by phase conjugation," Optics Express 18, No. 4, Feb. 15, 2010, 3444.
Cui, X. et al., "Lensless high-resolution on-chip optofluidic microscopes for *Caenorhabditis elegans* and cell imaging," PNAS, vol. 105, No. 31, Aug. 5, 2008, 10670-10675.
Cui, M. et al., "Observation of polarization-gate based reconstruction quality improvement during the process of turbidity suppression by optical phase conjugation," Applied Physics Letters 95, 123702 (2009).
Debarre, D. et al., "Adaptive optics for structured illumination microscopy," Optics Express 16, No. 13, Jun. 23, 2008, 9290.
Debarre, D. et al., "Image-based adaptive optics for two-photo microscopy," Optics Letters, vol. 34, No. 16, Aug. 15, 2009, 2495.
Denk, W. et al., "Two-photon laser scanning fluorescence microscopy," Science 248(4951), 1990, 73.
Derode, A. et al., "Random multiple scattering of ultrasound. II. Is time reversal a self-averaging process?," Physical Review E, vol. 64, 2001, 036606.
Dougherty, T. et al., "Photodynamic therapy," Journal of the National Cancer Institute, vol. 90, No. 12, Jun. 17, 1998, 889.
Feinberg, J. et al., "Phase-conjugating mirror with continuous-wave gain," Optics Letters, vol. 5, No. 12, Dec. 1980, 519.
Fink, M., "Time reversed acoustics," Physics Today 50(3), 34-40 (1997).
Goodman, J., "Some fundamental properties of speckle," J. Opt. Soc. Am., vol. 66, No. 11, Nov. 1976, 1145.
Griffin, R. et al., "Use of a fluroescently labeled poly-casapase inhibitor for in vivo detection of apoptosis related to vascular-targeting agent arsenic trioxide for cancer therapy," Technology in Cancer Research and Treatment, vol. 6, No. 6, Dec. 2007, 651.
Haka, A. et al., "Diagnosing breast cancer by using Raman spectroscopy," PNAS, vol. 102, No. 35, Aug. 30, 2005, 12371-12376.
Hayden, E., "Microscopic marvels: Microscope for the masses," Nature, vol. 459, p. 632, 2009.
Hedlund, E. et al., "Malignant cell-derived PlGF promotes normalization and remodeling of the tumor vasculature," PNAS, vol. 106, No. 41, Oct. 13, 2009, 17505-17510.
Hell, S. et al., "Properties of a 4Pi confocal fluorescence microscope," J. Opt. Soc. Am. A, vol. 9, No. 12, Dec. 1992, 2159.
Huang, D. et al., "Optical coherence tomography," Science, vol. 254, Nov. 22, 1991, 1178.
Hyde, S. et al., "Depth-resolved holography through turbid media using photorefraction," IEEE Journal of Selected Topics in Quantum Electronics, vol. 2, No. 4, Dec. 1996, 965.
Leith, E. et al,. "Holographic imagery through diffusing media," Journal of the Optical Society of America, vol. 56, No. 4, Apr. 1966, 523.
Lind, R. et al., "Demonstration of the longitudinal modes and aberration-correction properties of a continuous-wave dye laser with a phase-conjugate mirror," Optics Letters 6, No. 11, Nov. 1981, 554.
Lindsay, I., "Specular reflection cancellation/enhancement in the presence of a phase-conjugate mirror," J. Opt. Soc. Am. B, vol. 4, No. 11, Nov. 1987, 1810.
McDowell, E. et al., "Turbidity suppression from the ballistic to the diffusive regime in biological tissues using optical phase," Journal of Biomedical Optics 15(2), 025004 (Mar./Apr. 2010).
Pepper, D., "Observation of diminished specular reflectivity from phase-conjugate mirrors," Physic Review Letters, vol. 62, No. 25, Jun. 19, 1989, 2945.
Primmerman, C. et al., "Compensation of atmospheric optical distortion using a synthetic beacon," Letters to Nature, vol. 353, Sep. 12, 1991, 141.
Ridley, K. et al., "Incomplete phase conjugation through a random phase screen. II. Numerical simulations," J. Opt. Soc. Am. A, vol. 13, No. 12, Dec. 1996, 2393.
Rueckel, M. et al., "Adaptive wavefront correction in two-photon microscopy using coherence-gated wavefront sensing," PNAS, vol. 103, No. 46, Nov. 14, 2006, 17137-17142.
Vellekoop, I. et al., "Demixing light paths inside disordered metamaterials," Optics Express 16, No. 1, Jan. 7, 2008, 67.
Vellekoop, I. et al., "Focusing coherent light through opaque strongly scattering media," Optics Letters 32, No. 16, Aug. 15, 2007, 2309.
Vellekoop, I. et al., "Universal optical transmission of light through disordered materials," Physical Review Letters 101, 120601 (2008).
Wang, L., "Multiscale photoacoustic microscopy and computer tomography," Nature Photonics, vol. 3, Sep. 2009, 503.
Wang, L. et al., "Ultrasound-mediated biophotonic imaging: A review of acousto-optical tomography and photo-acoustic tomography," Disease Markers 19 (2003, 2004) 123-138.
Wang, L. et al., "Ultrasound-modulated optical tomography of absorbing objects buried in dense tissue-simulating turbid media," Applied Optics 36, No. 28, Oct. 1, 1997, 7277.
Wenner, M., "The most transparent research," Nat. Med. 15(10), 1106-1109 (2009).
Xu, X. et al., "Time-reversed ultrasonically encoded optical focusing into scattering media," Nature Photonics, vol. 5, Mar. 2011, 154.
Yamaguchi, I., "Phase-shifting digital holography," Optics Letters 22, No. 16, Aug. 15, 1997, 1268.
Yariv, A., "Phase conjugate optics and real-time holography," IEEE Journal of Quantum Electronics, vol. QE-14, No. 9, Sep. 1978, 650.
Yaqoob, Z. et al., "Optical phase conjugation for turbidity suppression in biological samples," Nature Photonics, vol. 2, Feb. 2008, 110.
Yuan, B. et al., "Ultrasound-modulated fluorescence from rhodamine B aqueous solution," Journal of Biomedical Optics 15(2), 021321 (Mar./Apr. 2010).
Zhang, T., "Three-dimensional microscopy with phase-shifting digital holography," Optics Letters 23, No. 15, Aug. 1, 1998, 1221.
Fink, M., "Time-reversed acoustics," Sci. Am. 281(5), 91-97 (1999).
Gower, D., *Optical phase conjugation*, 1994, New York: Springer-Verlag, copyright and table of contents only.
Vo-Dinh, T., *Biomedical photonics handbook*, 2003, New York: CRC press, copyright and table of contents only.
Wang, L. et al., *Biomedical optics: Principles and imaging*, 2007, Hoboken, New Jersey: Wiley-Interscience, copyright and table of contents only.
Yeh, P. *Introduction of photorefractive nonlinear optics*, 1993, New York: John Wiley & Sons, Inc., copyright and table of contents only.

* cited by examiner

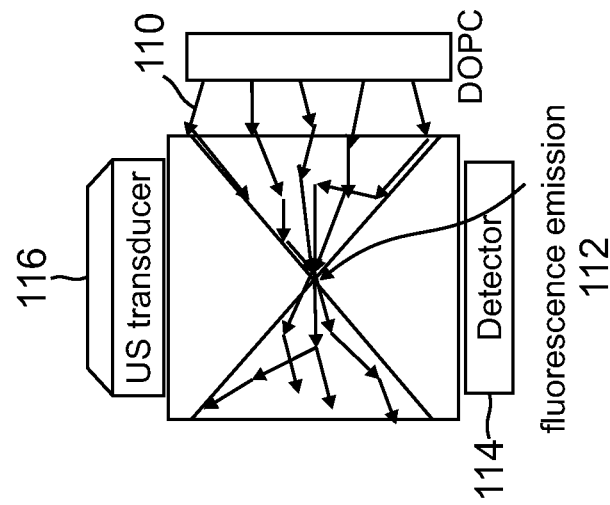
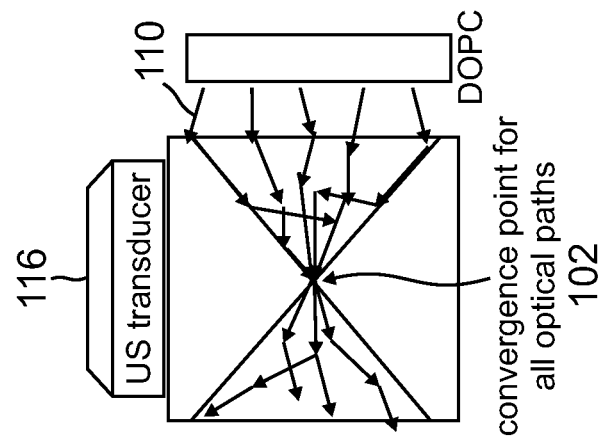
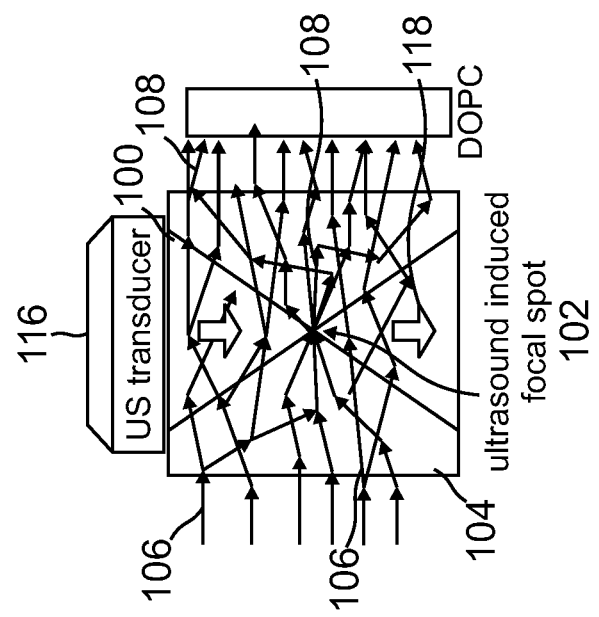

ACOUSTIC ASSISTED PHASE CONJUGATE OPTICAL TOMOGRAPHY

CROSS REFERENCE TO RELATED APPLICATIONS

This application claims the benefit under 35 U.S.C. 119(e) of the following co-pending and commonly-assigned U.S. provisional patent applications, which are incorporated by reference herein:

Provisional Application Ser. No. 61/355,328, filed on Jun. 16, 2010 by Meng Cui, Ying Min Wang and Changhuei Yang, entitled "ACOUSTIC ASSISTED PHASE CONJUGATE OPTICAL TOMOGRAPHY,";

Provisional Application Ser. No. 61/259,975, filed on Nov. 10, 2009, by Changhuei Yang and Meng Cui, entitled "APPROACHES FOR BUILDING COMPACT FLUORESCENCE MICROSCOPES,"; and Provisional Application Ser. No. 61/260,316, filed on Nov. 11, 2009, by Changhuei Yang and Meng Cui, entitled "APPLICATIONS OF TURBIDITY SUPPRESSION BY OPTICAL PHASE CONJUGATION,"; and Provisional Patent Application Ser. No. 61/376,202, filed on Aug. 23, 2010, by Meng Cui and Changhuei Yang, entitled "OPTICAL PHASE CONJUGATION 4PI MICROSCOPE,".

This application is related to the following co-pending and commonly-assigned U.S. patent applications, which are incorporated by reference herein:

U.S. Utility Patent Application Ser. No. 12/886,320, filed on Sep. 20, 2010, by Zahid Yaqoob, Emily McDowell and Changhuei Yang, entitled "OPTICAL PHASE PROCESSING IN A SCATTERING MEDIUM,", which application is a divisional of U.S. Utility Patent Application Ser. No. 11/868,394, filed on Oct. 5, 2007, by Zahid Yagoob, Emily McDowell and Changhuei Yang, entitled "TURBIDITY ELIMINATION USING OPTICAL PHASE CONJUGATION AND ITS APPLICATIONS,", which application claims priority under 35 U.S.C. §119(e) to commonly-assigned U.S. Provisional Patent Application Ser. No. 60/850,356, filed on Oct. 6, 2006, by Zahid Yaqoob, Emily McDowell and Changhuei Yang, entitled "TURBIDITY ELIMINATION USING OPTICAL PHASE CONJUGATION AND ITS APPLICATIONS,".

U.S. Utility Application Ser. No. 12/943,857, filed on same date herewith, by Chenghuei Yang and Meng Cui, entitled "TURBIDITY SUPPRESSION BY OPTICAL PHASE CONJUGATION USING A SPATIAL LIGHT MODULATOR,", which application claims priority under 35 U.S.C. §119(e) to co-pending and commonly-assigned U.S. Provisional Application Ser. No. 61/259,975, filed on Nov. 10, 2009, by Changhuei Yang and Meng Cui, entitled "APPROACHES FOR BUILDING COMPACT FLUORESCENCE MICROSCOPES,", U.S. Provisional Application Ser. No. 61/260,316, filed on Nov. 11, 2009, by Changhuei Yang and Meng Cui, entitled "APPLICATIONS OF TURBIDITY SUPPRESSION BY OPTICAL PHASE CONJUGATION,"; U.S. Provisional Application Ser. No. 61/355,328, filed on Jun. 16, 2010 by Meng Cui, Ying Min Wang and Changhuei Yang, entitled "ACOUSTIC ASSISTED PHASE CONJUGATE OPTICAL TOMOGRAPHY,"; and Provisional Patent Application Ser. No. 61/376,202, filed on Aug. 23, 2010, by Meng Cui and Changhuei Yang, entitled "OPTICAL PHASE CONJUGATION 4PI MICROSCOPE,"; and U.S. Utility Application Ser. No. 12/943,818, filed on same date herewith, by Meng Cui and Changhuei Yang, entitled "OPTICAL PHASE CONJUGATION 4PI MICROSCOPE,", which application claims priority under 35 U.S.C. §119(e) to co-pending and commonly-assigned U.S. Provisional Application Ser. No. 61/376,202, filed on Aug. 23, 2010, by Meng Cui and Changhuei Yang, entitled "OPTICAL PHASE CONJUGATION 4PI MICROSCOPE,"; U.S. Provisional Application Ser. No. 61/259,975, filed on Nov. 10, 2009, by Changhuei Yang and Meng Cui, entitled "APPROACHES FOR BUILDING COMPACT FLUORESCENCE MICROSCOPES,", U.S. Provisional Application Ser. No. 61/260, 316, filed on Nov. 11, 2009, by Changhuei Yang and Meng Cui, entitled "APPLICATIONS OF TURBIDITY SUPPRESSION BY OPTICAL PHASE CONJUGATION,"; and U.S. Provisional Application Ser. No. 61/355,328, filed on Jun. 16, 2010 by Meng Cui, Ying Min Wang and Changhuei Yang, entitled "ACOUSTIC ASSISTED PHASE CONJUGATE OPTICAL TOMOGRAPHY,".

STATEMENT REGARDING FEDERALLY SPONSORED RESEARCH AND DEVELOPMENT

This invention was made with Government support under Grant No. R21EB008866-02 awarded by the National Institutes of Health. The Government has certain rights in this invention.

BACKGROUND OF THE INVENTION

1. Field of the Invention

This invention relates to acoustic assisted phase conjugate optical tomography.

2. Description of the Related Art (Note: This application references a number of different publications as indicated throughout the specification by one or more reference numbers within brackets, e.g., [x]. A list of these different publications ordered according to these reference numbers can be found below in the section entitled "References." Each of these publications is incorporated by reference herein.)

Deep-tissue clinical imaging techniques, such as ultrasound, magnetic resonance imaging (MRI) and X-ray imaging, provide clinicians with the means to visualize the interior structures of the scanned subject. While these methods are excellent at rendering contrast based on the structural characteristics of the tissues, their general limited ability to perform biochemical imaging poses a significant limitation to their realizable diagnostic potentials. As an example, consider the case of mammography screening for breast cancer. In such screenings, the clinician looks for suspicious lesion masses in the X-ray images. It is often difficult to judge if a mass is simply a benign calcified accumulation or a developing tumor [1]. To arrive at a conclusive diagnosis, a biopsy is required to surgically remove part of the tissues from the mass for further analysis. An imaging method that can provide additional biochemical information, such as HER2 (human epidermal growth factor receptor 2) presence or relative fat content [1], can dramatically improve the accuracy of such pre-biopsy analysis. More importantly, these biochemical changes can in principle be measured at an earlier progression stage that precedes formation of structural anomalies that are detectable by ultrasound, MRI and X-ray. The same consideration also applies for the screenings of cancer of the other organs, such as the prostate, liver, lungs and brain.

Similarly, the amount of real-time, in vivo information obtainable in vertebrate animal models by current methods is also limited. A high resolution, non-invasive, deep tissue imaging method would facilitate in vivo studies that may provide more insight to tissue and organ system development, disease progression and disease regression in the presence of therapeutics.

Optical methods offer excellent means for biochemical sensing. There is a wealth of light-matter interaction mechanisms, such as fluorescence [2], absorption [3], Raman scattering [1], as well as nonlinear light interactions [4], which can be used to perform biochemical specific sensing and measurements.

Despite the biochemical sensing advantage, the conventional optical methods are unable to accomplish optical imaging with a resolution better than 100 microns in tissues that are thicker than a couple of millimeters. Optical-based deep tissue imaging is largely impeded by the fact that biological tissues scatter light very strongly. As a point of reference, the mean scattering length of 633 nm light in dermis is 50 microns, while the mean absorption length is 3.7 mm [5]. Much like the case of fog, tissue turbidity obscures the line of sight by diffusing light and preventing the forming of an optical focus.

In recent years, several biophotonics imaging approaches have been developed to push the optical imaging depth limit. Here is a summary of some of the more promising approaches:

1. Optical Coherence Tomography (OCT) [6]. OCT has excellent resolution (~ microns) but relatively limited imaging depth (typically 1 mm). Additionally, OCT renders mostly structural information-based or flow-based images and is not well suited to collect fluorescence or Raman information.

2. Diffuse optical tomography (DOT) [7]. This approach comprises a wide range of techniques and innovations. Broadly speaking, DOT sends light through the target tissue and carefully measures the resulting transmission from a number of exit points. DOT then renders a relatively low resolution 'best-guess' image of the tissue. DOT can work with thick tissues, but its resolution is fairly low (>1 mm). The biochemical-associated information collected is largely absorption spectrum based.

3. Ultrasound-modulated optical tomography (UOT) [8]. In this method, an ultrasound beam is brought to a focus within the target tissue which is illuminated by light. The transmitted light field will carry a modulated component, which correlates to the light field component that has passed through that ultrasound focal point. By scanning the ultrasound focus through the tissue and measuring the modulation strength in the transmitted light field, an image of the sample can then be rendered. The imaging depth for such a strategy is high (~ cm) and the resolution corresponds to the ultrasound focal spot size (~10's to 100 microns). Unfortunately, the much sought modulation is associated with a high background signal that significantly degrades sensitivity.

4. Photoacoustic tomography (PAT) [3]. In PAT, the target tissue is illuminated with a pulsed laser source. The laser pulse is absorbed by absorbers in the tissue and induces rapid thermal-expansion at the absorber site. The generated acoustic waves are then detected and measured by an array of ultrasound transducer at the tissue's boundaries. This method has a large imaging depth (~1 cm) and the resolution achieved can also be high (~100 microns). The biochemical information gathered is largely absorption-based.

SUMMARY OF THE INVENTION

One or more embodiments of the present invention provide an imaging system (e.g., microscope or optical microscope) for imaging a sample, comprising one or more sources of one or more signals, wherein the signals propagate to one or more regions of the sample and modulate input light into modulated (e.g., frequency shifted) light, the input light is modulated (e.g., frequency shifted) into the modulated light as the input light passes through the one or more regions of the sample concurrently with the signals; a Digital Optical Phase Conjugation (DOPC) device including a sensor for detecting the modulated light inputted onto the sensor, and at least one spatial light modulator (SLM) positioned to illuminate the one or more regions with output light that is an optical phase conjugate of the modulated light, wherein the output light is a reflection of reference light from one or more pixels of the SLM, and the pixels modulate the reference light to create the output light in response to the modulated light detected by the sensor; and one or more detectors positioned to detect one or more resulting outputs that are based on an interaction between the output light and the one or more regions of the sample, thereby imaging the sample.

The one or more signals may comprise one or more acoustic waves generated by one or more acoustic wave sources.

The output may comprise fluorescence generated by the output light exciting fluorescent agents in the one or more regions, thereby imaging the sample.

The acoustic waves may be focused at a single focus or single focal point in the sample, so that the one or more regions are a single focal spot or focus. The detector may be positioned to detect a threshold fraction of the fluorescence from the focal spot so that a fluorescence concentration at the focal spot is measured.

The imaging system may further comprise a translation stage for moving the focus with respect to the sample so that a plurality of foci are produced within the sample, wherein the detector detects the resulting outputs at each of the foci, thereby mapping a fluorescence concentration distribution across the sample.

The output light may excite the fluorescence that is two-photon fluorescence.

The fluorescent agents may be photosensitizing agents that induce biochemical reactions only at the focal spot in response to excitation by the output beam only at the focus, thereby performing photodynamic therapy.

The acoustic waves may modulate the input light by frequency shifting a frequency of the input light by a single frequency f of the acoustic waves, or by multiples of f.

The imaging system may be used in optical coherence tomography to image the sample using the output light.

The outputs may be used to measure aberrations or distortions to the input light caused by the sample in the regions around the focus, and the imaging system corrects for the aberrations or distortions.

The microscope or imaging system may further comprise a source of the input light and the SLM positioned such that at least part of the input light is transmitted through the sample and the focus, and the modulated or frequency shifted light beam is collected by the sensor in the DOPC device in a transillumination configuration.

The DOPC device may include a source of the light positioned such that at least part of the input light is transmitted through the sample, and the modulated or frequency shifted light beam is backscattered towards the DOPC device and collected by the DOPC device.

The microscope or imaging system may further comprise a beam splitter positioned to direct the modulated or frequency shifted light beam, and transmit a second reference beam or light, to the sensor so that the modulated light or frequency shifted light beam and the second reference beam interfere and produce interferometric data that is used to calculate the optical phase conjugate of the frequency shifted light beam or modulated light that is outputted by the SLM.

The microscope or imaging system may further comprise a source of the reference light (e.g., first reference beam), wherein the SLM outputs the output beam that is a reflection of the first reference beam directed onto the pixels of the SLM by a beamsplitter; and one or more computer processors for controlling the first reference beam's output power such that an output power of the output beam or output light is sufficient to excite the fluorescence detected by the detector; synchronizing the acoustic waves to the output beam or light; and controlling a power of the acoustic waves to optimize efficiency of the frequency shifting or modulation.

The DOPC may have an update rate faster than time scales of one or more movements in living tissues that deteriorate the TSOPC reconstruction efficiency.

The imaging system or microscope may comprise an objective or lens to focus the acoustic waves such that the focus has a diameter of 100 micrometers or less and/or such that the focus is at a depth of at least 1 centimeter below a surface of the sample.

The present invention further discloses a method for imaging a sample, comprising propagating, from one or more sources, one or more signals to one or more regions of the sample; modulating (e.g., frequency shifting) input light into modulated (e.g., frequency shifted) light, wherein the input light is modulated into the modulated light as the input light passes through the one or more regions of the sample concurrently with the signal; detecting, on a sensor, the modulated light inputted onto the sensor, illuminating the one or more regions with output light outputted from at least one spatial light modulator (SLM), wherein the output light that is an optical phase conjugate of the modulated light, the output light is a reflection of reference light from one or more pixels of the SLM, and the pixels modulate the reference light to create the output light in response to the modulated light detected by the sensor; and detecting one or more resulting outputs that are based on an interaction between the output light and the one or more regions of the sample, thereby imaging the sample.

One or more of the signals may comprise one or more acoustic or ultrasound waves generated by one or more acoustic wave sources or ultrasound sources.

The method may further comprise generating fluorescence by the output light exciting fluorescent agents in the one or more regions, thereby imaging the sample, wherein the outputs are the fluorescence.

The method may comprise focusing the acoustic waves at a single focus, focal point or focal spot in the sample so that the one or more regions are the single focal spot or focus or point.

The method may comprise positioning the detector to detect a threshold fraction of the fluorescence from the focal spot so that a fluorescence concentration at the focal spot is measured.

The method may comprise moving the focus with respect to the sample so that a plurality of foci are produced within the sample, wherein the detector detects the resulting outputs at each of the foci, thereby mapping a fluorescence concentration distribution across the sample.

The method may further comprise selecting a wavelength of the output light excites the fluorescence that is two-photon fluorescence, thereby imaging the sample using two-photon fluorescence.

The method may further comprise performing photodynamic therapy by using the fluorescent agents as photosensitizing agents that induce biochemical reactions only at the focal spot in response to excitation by the output beam only at the focus.

The method may further comprise using the acoustic waves to modulate the input light by frequency shifting a frequency of the input light by a single frequency of the acoustic waves.

The method may further comprise using the imaging system to perform optical coherence tomography to image the sample using the output light.

The method may further comprise generating, from a source, the acoustic waves that are focused at the focus; modulating a first reference beam to create the output beam or light, wherein the output beam or light is a reflection of a first reference beam off one or more pixels of the SLM; and detecting fluorescence generated by the output beam or light that has retraced the path and excited the fluorescent agents at the focus in the sample, thereby imaging the sample.

The method may further comprise detecting, on a sensor, the frequency shifted light beam, wherein the SLM outputs the output beam in response to the frequency shifted light beam detected by the sensor and the SLM and the sensor are included in a Digital Optical Phase Conjugation (DOPC) device.

The method may further comprise transmitting the input light through the sample and the focus such that the modulated or frequency shifted light beam is collected by the sensor in the DOPC device in a transillumination configuration.

The method may further comprise illuminating, from a source included in the DOPC device, the sample such that at least part of the input light is transmitted through the sample, and the modulated or frequency shifted light beam is backscattered towards the DOPC device and collected by the DOPC device.

The method may further comprise directing, using a beam splitter, the modulated or frequency shifted light beam to the sensor; and transmitting, through the beam splitter, a second reference beam to the sensor so that the modulated or frequency shifted light beam and the second reference beam interfere and produce interferometric data that is used to calculate the optical phase conjugate of the frequency shifted light beam that is outputted by the SLM.

The method may further comprise generating the first reference beam from a source; directing, using a beamsplitter, the first reference beam onto the pixels of the SLM so that the SLM outputs the output beam or light; controlling, using one or more processors, the first reference beam's output power such that an output power of the output beam or output light is sufficient to excite the fluorescence detected by the detector; and synchronizing, using the processors, the acoustic waves to the output beam or output light; and controlling, using the processors, a power of the acoustic waves to optimize efficiency of the modulation or frequency shifting.

If the sample is living tissue, the method may further comprise updating the DOPC device faster than one or more time scales of one or more movements in the living tissue that deteriorate a Turbidity Suppression by Optical Phase Conjugation (TSOPC) reconstruction efficiency.

The method may further comprise performing photodynamic therapy, wherein the fluorescent agents are photosensitizing agents that induce biochemical reactions only at the focus in response to excitation by the output beam only at the focus.

BRIEF DESCRIPTION OF THE DRAWINGS

Referring now to the drawings in which like reference numbers represent corresponding parts throughout:

FIG. 1 are cross-sectional schematics of a deep tissue optical focusing method according to one or more embodiments of the present invention, wherein in FIG. 1(a) the present invention uses an ultrasound transducer (frequency=f) to focus acoustic power to a desired spatial point, and arranges for the digital optical phase conjugation (DOPC) system to lock onto and record the light field components (shifted by f) that have passed through that focal point, FIG. 1(b) shows the DOPC can generate a time-reversed light field copy that can retrace its trajectories through that focal point—effectively focusing the light onto that point, FIG. 1(c) illustrates this focal point can be used to excite fluorophores for imaging purposes.

FIG. 2 is a schematic illustrating the experimental scheme of the DOPC system according to one or more embodiments of the present invention, the DOPC system comprising a spatial light modulator (SLM) and an electro-optic modulator (EO), wherein FIG. 2(a) illustrates the DOPC in wavefront sensing mode and FIG. 2(b) illustrates the DOPC in SLM playback mode.

FIG. 6(b) illustrates the DOPC generating a light field that passes through a focal point—effectively focusing light onto that point, FIG. 6(c) shows that the focal point can be used to excite fluorophores for imaging purposes, and FIG. 6(d) shows the focal point can also be used to locally excite PDT agent deep within the tissue;

DETAILED DESCRIPTION OF THE INVENTION

Figure 2:
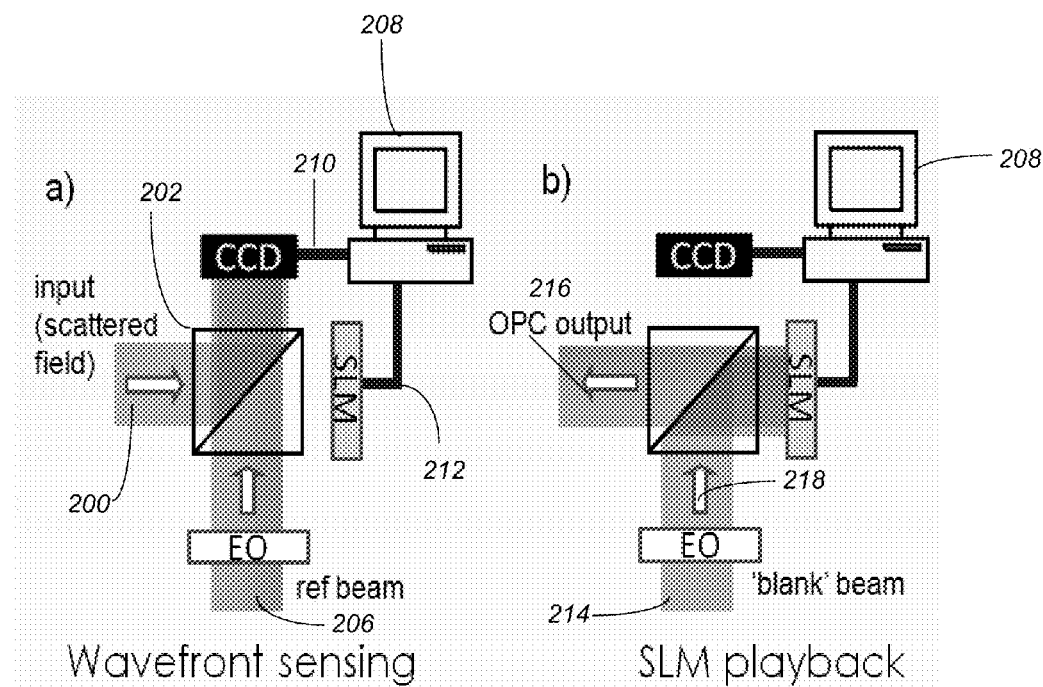

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Overview

Despite the rapid progress in biomedical optics in the past few decades, high tissue turbidity in the optical domain remains a difficult challenge that impedes high-resolution deep optical tissue imaging. Due to elastic scattering, conventional fluorescence imaging methods are severely limited in imaging depth (typically hundreds of microns at most). Fundamentally, the problem lies in the fact that it is not possible to focus light tightly in deep tissues using conventional optics.

Focusing light in a scattering medium is not an impossible proposition. Simplistically speaking, if the present invention has full knowledge of the positions and scattering profile of the scattering sites within the scattering medium, it would be possible to tailor the wavefront of an incident light field to optimally couple light to any specific point in the tissue. This approach capitalizes on the fact that scattering is a deterministic process. Unfortunately, the high complexity of typical tissues prevents the full characterization of the tissue with sufficient detail and within an adequately short time frame to accomplish such wavefront tailoring.

Embodiments of the present invention provide a novel acousto-optical method that permits optical focusing in deep tissues. A time-reversed light field, as generated by optical phase conjugation (OPC), can retrace its trajectory through tissue and undo the effects of scattering; a phenomenon termed turbidity suppression by optical phase conjugation (TSOPC).

Embodiments of the invention combine the TSOPC phenomenon with the use of ultrasound modulation to create an optical focus (diameter≦100 microns) that can be arbitrarily positioned within a thick tissue (5 millimeters or more). Schematically, the optical focus may be created as follows. An ultrasound transducer may be used to generate an ultrasound focus through the tissue. A light beam is transmitted through the tissue. The light beam scatters and diffuses through the tissue, but some of the light passes through the ultrasound focus and becomes frequency-upshifted by absorbing a phonon. By detecting and generating an OPC copy of the transmitted frequency-shifted light field, a light field is sent back through the tissue that converges at the ultrasound focus. In such a way, the ultrasound focus is used to guide the optical wave. The optical focus can be guided to any point within the tissue by tuning the ultrasound focus to that point.

This optical focus may then be used for imaging or phototherapeutic purposes. For example, this optical focus can be used to excite fluorophores at its locality. By raster-scanning the optical focus (via raster-scanning the ultrasound focus), fluorescence imaging may be performed at a combination of depth and resolution that is beyond the reach of conventional optical imaging methods. Besides fluorescence, this method can also work with absorption or Raman emission as contrast. The optical focus can also be used to activate photodynamic therapy agents locally.

Embodiments of the present invention represent a novel way to tackle tissue scattering and can potentially allow development of a hybrid ultrasound-optical deep tissue imaging technology, with which tissues may be imaged with resolution and depth penetration comparable to ultrasound, and with biochemical specificity that is provided by optical interrogation.

Such an imaging method may benefit biomedical studies where in vivo deep tissue imaging is required to observe gene expression, metabolism, and other physiological processes in real-time and three-dimension. The highly versatile nature of the optical-based imaging methods combined with the ability to penetrate deep into tissues may also be a valued addition to the suite of clinical imaging methods. Further, disease diagnoses may be transformed. Such a method can help a clinician to better assess the cancer potential of suspicious lesions during breast cancer and prostate screenings by providing biochemical information non-invasively.

Embodiments of the present invention further disclose a method to verify the ability to bring light to a focus. A resolution of 100 microns at a depth of ~5 mm within a tissue phantom is targeted.

Embodiments of the present invention further describe a method to map out the operating parameter space associated with the method.

Embodiments of the present invention further describe a method of imaging a fluorescence target within a tissue phantom with a resolution of 100 microns or better, and a method to image a fluorescently-tagged tumor within a living mouse with 100 microns resolution and penetration depth of 5 mm or more.

Technical Description

Concept

Embodiments of the present invention disclose an optical focusing method that uses ultrasound to help focus light within the tissue target to accomplish high-resolution (100 microns or less) deep tissue optical imaging (to a depth of at least 5 mm). The method may build upon the use of time-reversal techniques to suppress tissue scattering to induce a limited form of transparency.

FIG. 1(a)-(c) illustrate the new imaging scheme of the present invention, based on TSOPC.

FIG. 1(a) illustrates how embodiments of the present invention first tightly focus an ultrasound wave 100 of frequency f into a spot 102 of interest within the tissue 104. Since the ultrasound wave 100 experiences comparatively weaker scattering in tissues 104 than the optical transmission, a well-defined ultrasound focal spot 102 of dimension ~100 microns or better is created deep within the tissue.

Next, a weak light beam 106 (scouting field) is transmitted through the sample 104. A portion of the photons 108 that pass through the ultrasound focal zone, or ultrasound induced focal spot 102 are frequency upshifted or downshifted by f (due to absorption or stimulated emission of an ultrasound phonon). Photons passing through other regions where the ultrasound wave is traversing may also be frequency shifted, but the upshift may be most efficient within the focal zone 102 (where the ultrasound intensity is highest). (A related approach—ultrasound modulated optical tomography [13] detects these photons to determine tissue absorption at that location.)

Embodiments of the present invention may then apply a DOPC system (DOPC) to record the light field pattern of these transmitted upshifted photons 108. This may be accomplished by upshifting the reference beam of the wavefront sensing system by the ultrasound frequency so that the reference beam only interacts interferometrically with the upshifted transmission component.

By playing back a high intensity OPC field 110 (focusing field) based on this set of data, as illustrated in FIG. 1(b), photons can be sent back along the optical paths that intersect with the focal zone 102, which is the convergence point for all optical paths. In effect, this methodology offers a way to focus light at an arbitrarily definable location 102 within the tissue. The ultrasound waves 100 are simply focused at the location of interest 102 and the system channels the light into that location.

This system described herein is unique in at least two ways. First, the system provides an unprecedented ability to focus light at deep locations (potentially to depths of ~ cm's and a focal zone of dimension ~100 microns; there is a trade-off between depth and resolution) within tissues. Tissue scattering typically limits a conventional focusing system's (such as a simple lens) ability to focus light within tissue to a couple of mm's at best. Second and more importantly, this focal spot can be moved and scanned freely within the tissue by maneuvering the ultrasound focal spot accordingly.

FIG. 1(c) illustrates measuring the fluorescence emission 112 at the spot 102 using a detector 114. Also shown in FIG. 1(a)-(c) is the ultrasound transducer 116 for generating the ultrasound waves 100 along direction 118. By shifting the ultrasound focus 102 and repeating the steps illustrated in FIGS. 1(a)-(c) across the tissue 104, a fluorescence image can be collected. In one example, the focal spot 102 can be raster scanned within the tissue 104 and measures either the spontaneous Raman signal or the fluorescence emission 112 generated for each spot location, and then creates a biochemical image of the tissue 104. Preliminary results indicate that, as a start, this method is quite feasible for tissue of thickness up to ~2 cm (torso thickness of a mouse). This approach may be useful for small animal studies where biochemical changes can be imaged and mapped with good resolution. In addition, this method may be usable for tissue of greater thickness.

In one or more embodiments of the invention, the proportion of ultrasound frequency upshifted photons may be too low and the application of ultrasound may introduce undesirable vibrations in the tissue that can negative impact on the TSOPC effect. Accordingly, embodiments of the invention may select the ultrasound power input and the tissue thickness carefully. Based thereon, a hybrid ultrasound and optical imaging modality may be available for providing biochemical imaging capability with an ultrasound-type resolution and penetration.

Experimental Results

The next few paragraphs briefly discuss experimental results and elaborate on their relevance to embodiments of the present invention.

Turbidity Suppression by Optical Phase Conjugation (TSOPC)

The ability of a time-reversed light field to undo the effects of scattering is well known in the physics community and it has been demonstrated to work with distorted glass plates [13]. Specifically, if one records the phase and amplitude of the propagating scattered light field completely, it is possible to reproduce a back propagating optical phase conjugate (OPC) or time-reversed field. This field retraces its trajectory through the scattering medium and returns the original input light field. Embodiments of the present invention adapt the concept to suppress tissue scattering [9] and terms the phenomenon turbidity suppression by optical phase conjugation (TSOPC). Conceptually, this phenomenon is important because it implies that full and complete knowledge of the location and scattering profiles of the scattering sites in the medium is not required to accomplish scattering reversal. As long as the scattering profile of the exiting light field can be measured, scattering suppression can be accomplished.

TSOPC Through Thick Tissue Sections

The ability of TSOPC through chicken tissue sections up to 10 mm thick at the wavelength of 532 nm can be demonstrated. One can also experimentally verify that TSOPC is responsible for the reconstruction by observing that each spot disappears if the tissue section is displaced during the playback process.

Embodiments of the present invention have measured the tissue scattering coefficient to be 30.3 $mm^{-1}$ at this wavelength in a separate experiment. This result implies that, on average, a photon is scattered more than 300 times in the 10 mm thick tissue section. The thickness of the 10 mm section and the size of the phase conjugate mirror (a photorefractive crystal for this experiment) also imply that <0.02% of the available wavefront is only recorded. Yet, the time-reverse playback of this incomplete wavefront is capable of TSOPC reconstruction, albeit with a diminished efficiency. This experimental result points to the robustness of the phenomenon and its tolerance to information loss. Finally, it is worth noting that the reconstructed spot size remains the same for different tissue section thickness [12].

TSOPC in Living Tissues

One application of embodiments of the present invention is to image living targets. As such, one may first need to verify that the TSOPC phenomenon is stable when living tissues are involved. Specifically, one may need to know how quickly the positions of the scatterers will be perturbed within the living tissues.

To answer these questions, the TSOPC experiments can be performed through a live rabbit ear [11]. The scattering medium in this study is a shaved ear (~1 mm thick) of a New Zealand rabbit. To separate different mechanisms which can perturb tissue scattering, the TSOPC experiments can be performed while a rabbit is alive, and 0.5, 2, 24 hours after a rabbit is euthanized.

Several mechanisms can perturb the tissue scattering. First, the heart beat causes tissue vibration and bulk motion, which can move the tissue to a much greater length scale than the optical wavelength. Second, the cells are functioning in live tissues undergoing active processes, and they vary their shape, size, and location over time. Third, living tissues are semi-fluidic media. The Brownian motion of the particles in the tissues can alter the tissue scattering over time. All of these factors can significantly perturb the TSOPC signal, and each of them has its own time scale. An exponential function $a \cdot \exp(-t/\tau)$ was used to fit the decay and yield the decay constant, $\tau$. This decay constant is 1.5 seconds for the living rabbit ear tissue and 32 seconds for the tissue 24 hours post-death. This set of experiments showed that the movements in living tissues can deteriorate the TSOPC reconstruction efficiency. Thus, embodiments of the present invention may require recording and playback of the time-reversed wavefront to be within a time frame of <0.1 sec (shorter than the 1.5 sec decay constant) in order to image these living tissues. At these speeds, one does not expect living tissue movements to significantly impact the TSOPC reconstruction efficiency.

Digital Optical Phase Conjugation (DOPC)

The technology of OPC was originally developed in the field of nonlinear optics. The generation of phase conjugation field has traditionally relied on various nonlinear effects, such as the photorefractive effect, optical Kerr effect and stimulated Brillouin scattering. Generally, the OPC reflectivity, defined as the power ratio of the generated OPC wave to the input signal, is fairly low (significantly less than unity). However, in some applications, one may need an OPC system that is capable of recording a weak light field and that is capable of generating a strong time-reversed light field during the playback process (to adequately excite the fluorophores in the focal volume). Recently, an all-optoelectronics system may be developed with such a capability [10]. This system takes two separate steps to generate the phase conjugate fields, as shown in FIG. 2(a) and FIG. 2(b).

In step 1, a digital holography system is used to measure the amplitude and phase variations of the target light field of an input or beam 200 (wavefront sensing, as illustrated in FIG. 2(a)). A beam splitter 202 is positioned to direct the target or input scattered light field of the input beam 200, and transmit a reference beam 206 to the sensor (e.g., CCD) so that the input beam 200 and the reference beam 206 interfere and form one or more holograms on the sensor (e.g., CCD), and the holograms include interferometric data. An electro-optic modulator EO controls a relative phase between the input beam 200 and the reference beam 206, so that the holograms include one or more phase shifted holograms.

One or more processors (e.g., a computer 208) receive 210 the interferometric data and determine one or more phases and one or more amplitudes of the input light fields of input light beam 200, from the interferometric data. The processors 208 also digitally modify or reverse the phases and the amplitudes to produce modified or reversed phases and modify or reversed amplitudes that are outputted 212 to a spatial light modulator (SLM).

In step 2, the SLM is used to modify a 'blank' light field of a reference or blank beam 214 into an appropriate phase conjugate light field copy (SLM playback, illustrated in FIG. 2(b)). In this step, the pixels of the SLM are positioned to reflect the blank beam 214 having the OPC output 216 with the reversed or modified phases and reversed or modified amplitudes that are the optical phase conjugates of the phases and the amplitudes of the input beam 200.

The OPC reflectivity can be adjusted freely by changing the power of the input 'blank' light field 214. This feature is crucially important to the proposed hybrid optical focusing method because the frequency-modulated component is often weak and a significant OPC gain is required to generate a sufficiently strong optical focus for fluorescence imaging. Arrows 218 indicate the directions of beams 200, 206, 214, and 216.

Accordingly, embodiments of the present invention provide an appropriate optical phase conjugation system that is well-suited for use in a deep tissue optical focusing system.

Measurement of Focus Depth

Embodiments of the present invention disclose an experiment to verify that light can be brought to a focus at a depth of at least 5 mm within a tissue phantom. Ultrasound focus is used to modulate the light wave that travels through the focus, and perform optical phase conjugation to reconstruct an optical focus at the position of the acoustic focus.

Figure 3:
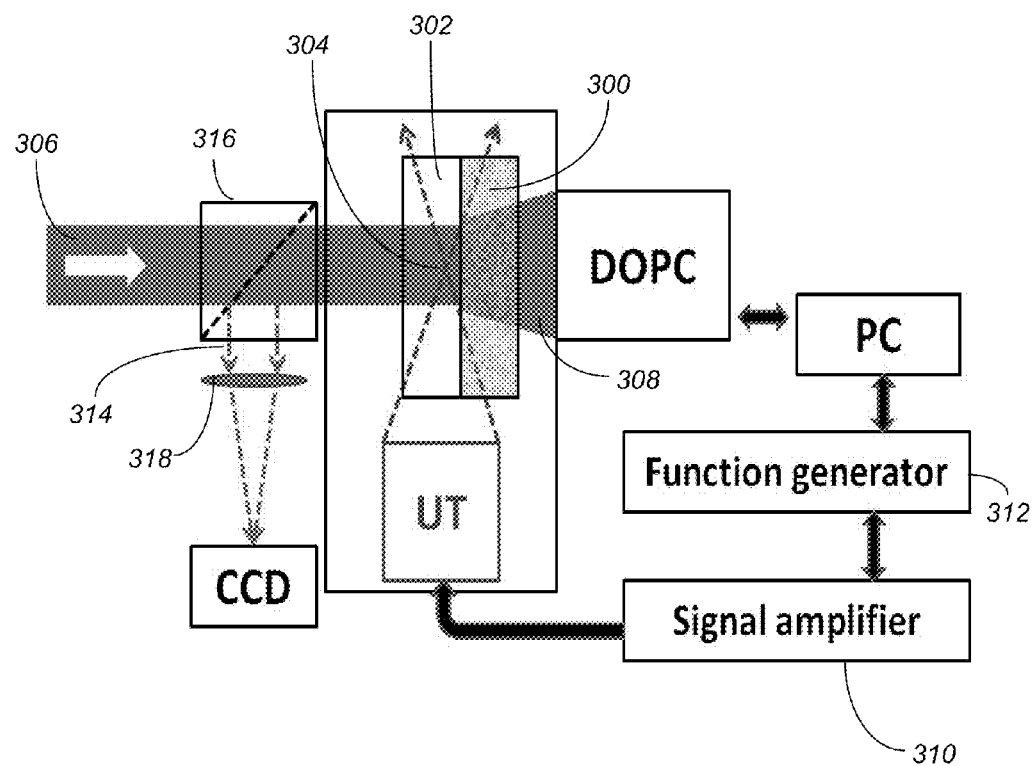
FIG. 3 is a schematic of an experimental setup for measuring the reconstructed optical focus through tissue phantoms, according to one or more embodiments of the present invention, and comprising ultrasound transducer (UT) and DOPC.

As the first step, the method is performed with tissue phantoms 300 of controllable scattering properties. The experiment scheme is shown in FIG. 3. As the goal of the experiment is to test whether an optical focus can be formed through a tissue phantom 300, the tissue phantom 300 is placed next to a transparent sample 302 made of similar hydrogel, and forms an acoustic focus 304 inside the transparent sample 302. In such a way, the reconstructed optical focus can be directly imaged onto a CCD camera (CCD).

Thus, FIG. 3 illustrates a method for verifying the thickness limit of an imaging beam in accordance with one or more embodiments of the invention. The method may comprise the following steps.

Step 1: illuminating the sample 302, 300 with a collimated laser beam 306 with ~1 cm in diameter (e.g., Crystal Laser Rubicon emitting light having a 532 nm wavelength, 20 ns pulse width, 1 kHz repetition rate, or SpectraPhysics Navigator emitting light having a 532-533, 532 nm wavelength, 7 ns pulse width, 20 kHz repetition rate, for example). An ultrasound focus 304 ~100 microns in diameter may be formed by a 15 MHz ultrasound transducer (UT), for example (e.g., a modified Olympus V313-SM), or 50 MHz ultrasound transducer, for example (e.g., Olympus V3330, for example). The present invention is not limited to these frequencies or wavelengths, light sources or transducers, however. The pulsing of the ultrasound wave may be synchronized with the laser pulsing. Light traveling through the focus may then experience a frequency shift. Some of the frequency-shifted light 308 may diffuse through the scattering tissue 300 phantom.

Step 2: Measuring the transmitted light in an interferometric measurement using a reference wave that is frequency shifted by exactly 50 MHz (by acousto-optic modulators). The reference beam is modulated using an acousto-optic modulator connected to a signal amplifier 310 connected to a function generator 312 connected to a computer or processor (e.g. PC). In such a way, the spatial phase profile, of the diffused frequency shifted light 308 that originates from the acoustic focus 304, may be acquired. To achieve this, the frequency shifted light 308 is inputted on a DOPC comprising the elements of FIG. 2

Step 3: Generating a phase conjugation wave with a sign-reversed phase profile (e.g., the DOPC comprising Boulder Nonlinear Systems #P512-0532 SLM may be used for this task). The phase conjugation wave may refocus through the scattering media at the acoustic focus 304.

Step 4: Directly imaging the reconstructed optical focus onto a CCD (CCD in FIG. 3) camera and quantitatively measuring the reconstructed focus. The focus may be imaged by guiding light 314 from the focus using a beamsplitter 316 and focusing the light 314 using a lens 318 on the CCD. Tissue phantoms 300 of different thickness may be used. With samples of different thickness (from 1 mm to 10 cm), the variation of the focus quality may be examined and the thickness limit of this method may be experimentally determined.

Mapping Out the Operating Parameter Space

Relevant parameters include: ultrasound focal spot size, ultrasound source power, and fraction of light field delivered through the focal spot.

To optimize the operating conditions of high-resolution (100 microns or less) deep tissue optical imaging, several important parameters may be experimentally determined.

The first parameter is the generated ultrasound focal spot size. To map out the focus, the following steps may be followed: mounting metal particles ~10 microns in diameter in a hydrogel sample and translating the metal particles in three dimensions around the focus while monitoring the ultrasound signal. In such a way, the ultrasound focus may be determined in three dimensions.

The second parameter is optimal ultrasound source power. Since the ultrasound modulation efficiency is not a simple linear function of the ultrasound power applied on the transducer, the optimal driving power may be experimentally determined. To achieve this goal, the following steps may be performed: directly forming an ultrasound focus in water and sending a collimated beam through the ultrasound focus. By comparing the power ratio of the measured frequency shifted light to the light that travels through the focus, the modulation efficiency may be determined. The measurements may be performed at various ultrasound driving powers to determine the optimal ultrasound power and the optimized modulation efficiency.

The target frequency and resolution of 100 microns represent various estimates. The findings of the mapping of parameter space may be used to modify the ultrasound frequency choice and the targeted resolution.

Imaging of a Fluorescence Target within a Tissue Phantom with Resolution of 100 Microns or Better The specified resolution and ultrasound frequency may be modified based on the findings from mapping of parameter space.

Figure 4:
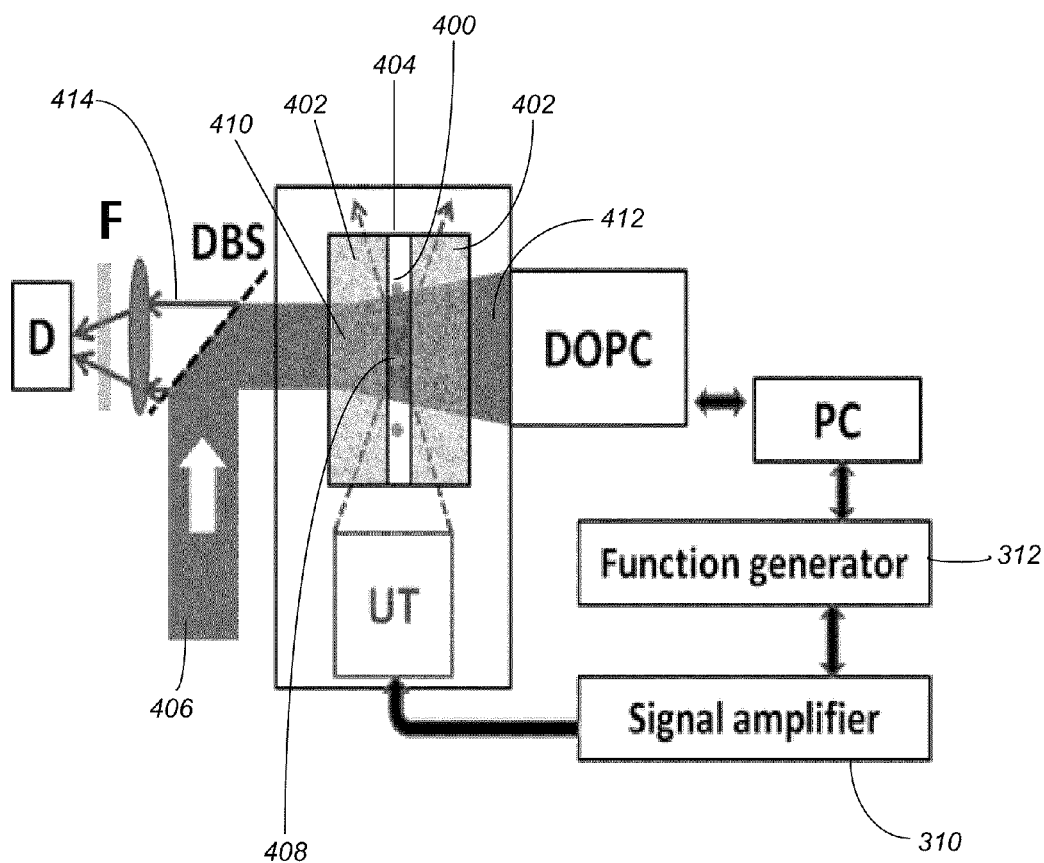
FIG. 4 is a schematic of an experimental setup for fluorescence imaging through tissue phantoms, according to one or more embodiments of the present invention, comprising dichroic beam-splitter (DBS), detector (D), and optical filter (F)

FIG. 4 is an experimental set up illustrating a method to enable fluorescence imaging through tissues. As a preliminary step, fluorescence targets 400 embedded in tissue phantoms 402 may be used as the sample in order to demonstrate this technique. For example, the sample may be prepared by first creating 100 micron wide and 100 micron deep wells on a PDMS (polydimethylsiloxane) layer 1 mm thick, adding a solution of Alexa-532 (a fluorescent dye with excitation/emission peaks of 532 nm/554 nm) on top of the PDMS layer to fill the created wells. The dye sample 404 may be sandwiched between two tissue phantoms 402 to mimic tissues.

FIG. 4 illustrates a method that comprises the following steps:

Step 1: Illuminating the sample 404 with a collimated laser beam 406 and generating an ultrasound focus 408 to modulate the diffused light 410.

Step 2: Measuring the phase profile of the transmitted modulated light 412 using a DOPC.

Step 3: Blocking the initial illumination beam 406, using phase conjugation (using the DOPC of FIG. 2) to produce an optical focus and measuring the excited fluorescence signal 414 from the sample 404.

At the end of the three steps, the sample 404 may be translated and the measurements may be repeated. In such a way, the present invention may perform three dimensional fluorescence imaging through tissues 402.

If the above steps are successful, embodiments of the present invention may use a modified scheme that utilizes the DOPC system to directly output a collimated laser beam to illuminate the sample in step 1. This converts the transillumination geometry (illustrated in FIG. 4) to a 'backscattering' geometry. As a sampling of the modulated scattered field is simply required, it should not matter if the collected field is in the forward or backward mode.

If the above steps are unsuccessful, the transillumination geometry may be applied in living tissue, as discussed in the next section.

The signal amplifier, function generator and PC are used to frequency modulate the reference beam. The reference beam is frequency modulated by an acousto-optic modulator (AOM) connected to a signal amplifier connected to a function generator. The ultrasound frequency signal generated by the function generator is amplified by the signal amplifier. The output signal is put into the AOM, frequency upshifting the light that passes through the AOM. The signal amplifier, function generator and PC are also used to provide an input signal to the ultrasound transducer.

Imaging Fluorescently-Tagged Tumors within Living Tissue with 100 Microns Resolution or Better and a Penetration Depth of 5 mm or More The specified resolution and ultrasound frequency may be modified based on the findings of mapping parameter space as discussed above.

Embodiments of the present invention may be utilized to perform tumor imaging, where much of the preclinical studies and clinical diagnosis can benefit from the deep tissue fluorescent imaging. Tumor imaging is of great importance both in the clinical assessment of cancer therapy outcomes and in preclinical studies. Optical imaging is a cost-effective, non-ionizing and versatile method to investigate the complex relationships between the tumor pathology and its structure and microenvironment. In vivo fluorescent imaging of tumors enables investigation of changes in structure and physiology during tumor development and in response to anticancer therapeutics. However, due to tissue scattering, sub-millimeter in vivo optical imaging of three-dimensional tumors remains a challenge. In preclinical models, solutions to the limited optical penetration depth include surgically accessing the imaging site and dorsal window chambers where tumors are essentially made to grow in a flat manner. These methods are highly invasive and thus have no potential to be transferable to clinical settings. Furthermore, they are fundamentally inadequate solutions even in the preclinical setting, since the tumors are subject to unnatural physiological settings and geometrical restrictions.

Embodiments of the present invention may address the abovementioned shortcomings. In this regard, embodiments of the present invention may be used to demonstrate the potential of the in vivo deep tissue fluorescent imaging ability, e.g., by imaging tumor vasculature in true three-dimensional solid tumors.

Subcutaneously tumors ~1 cm in diameter may be implanted and grown on the flanks of nude mice where their movement is minimally hindered. Using an imaging system, embodiments of the present invention may image the tumor vasculature by intravenous injection of Alexa-532-labeled dextran beads of varying molecular weight (circulatory half-life>24 hours).

The introduction of fluorescence probes may be performed according to published protocols [14, 15]. Nude mice are used because of the subcutaneous implantation and growth of tumor in this species is well studied and widely used. In one example, the present invention may use 7 nude mice in each of the 5 rounds of technical optimization iterations (total=35 mice). Mice may be anesthetized with isoflurane during the implantation of tumors and the injection of the contrast agent. During imaging, mice may be anesthetized with urethane (1 g/kg, I.P.) for a period longer than 2 hours, but not exceeding 4 hours.

Figure 5:
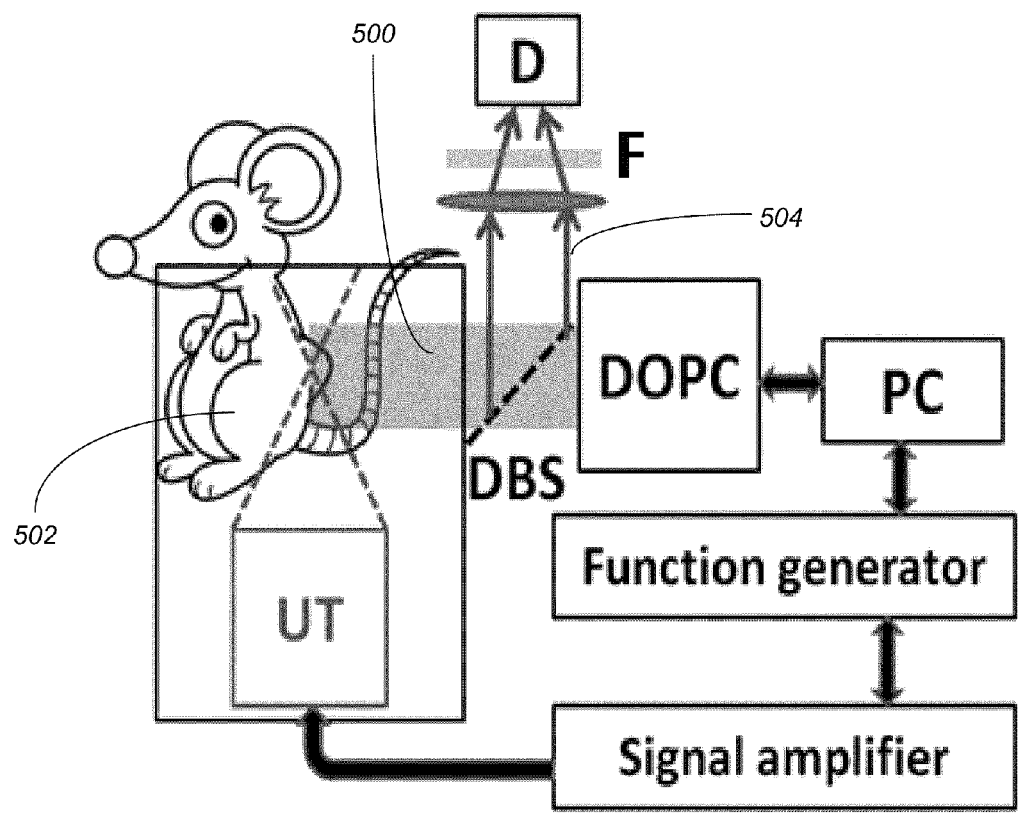
FIG. 5 is a schematic of an experimental setup for in vivo fluorescence imaging of tumors in nude mice, according to one or more embodiments of the present invention, comprising DBS, detector D, and optical filter F.

The imaging experiment setup is shown in FIG. 5. The imaging method may comprise directly using the DOPC system to output a laser beam 500 to illuminate the living tissue 502 (e.g., mouse tissue prepared above), and using a dichroic beamsplitter (DBS) to collect the back-propagating fluorescence signal 504 in the detector D. This is a "backscattering geometry".

If transillumination is more effective than a backscattering geometry for some applications, the method illustrated in FIG. 4 may be used to image the living tissue. The tumor implant may be pinched up between two glass slides to provide a transillumination path. The ultrasound focus of 30 microns in diameter produced by the 50 MHz ultrasound transducers should provide sufficient resolution to image regional apoptosis, venules and arterioles (~ typically 50-100 microns) as well as the larger blood vessels. The images obtained may be correlated to corresponding histological sections of the same tumor excised after the imaging is performed.

A challenge for in vivo imaging is that sample movement can perturb the phase conjugation process. The studies have shown that the time scale of the perturbation in an anesthetized rabbit is ~1.5 s. By using commercially available wavefront sensors (CCDs) and SLMs, the DOPC may have an update rate of ~70 Hz. At such a speed, the effect of sample movement may be greatly reduced. Using such commercially available devices, the DOPC may provide an update rate of ~70 Hz. At such a speed, the effect of sample movement can be greatly reduced. One may collect 100×100 pixel images in a time frame of ~2 minutes.

Improved Photodynamic Therapy

The TSOPC effect may also be applied to improve optical based therapeutic procedures, such as photodynamic therapy (PDT) [17]. In PDT, a photosensitizing agent, such as Photofrin, is introduced into the body and preferentially uptaken by cancer cells. Next, the tissue is illuminated with light to activate the photosensitizing agent. The resulting biochemical reactions then induce apoptosis of the cancer cells. The typical depth of necrosis with PDT is ~4 mm. Much of the delivered light does not penetrate through the tissue due to scattering. Furthermore, the procedure is fairly indiscriminate in its light delivery—the specificity of the treatment is almost entirely dependent on preferential uptake of the PDT agent by cancer cells.

Figure 6:
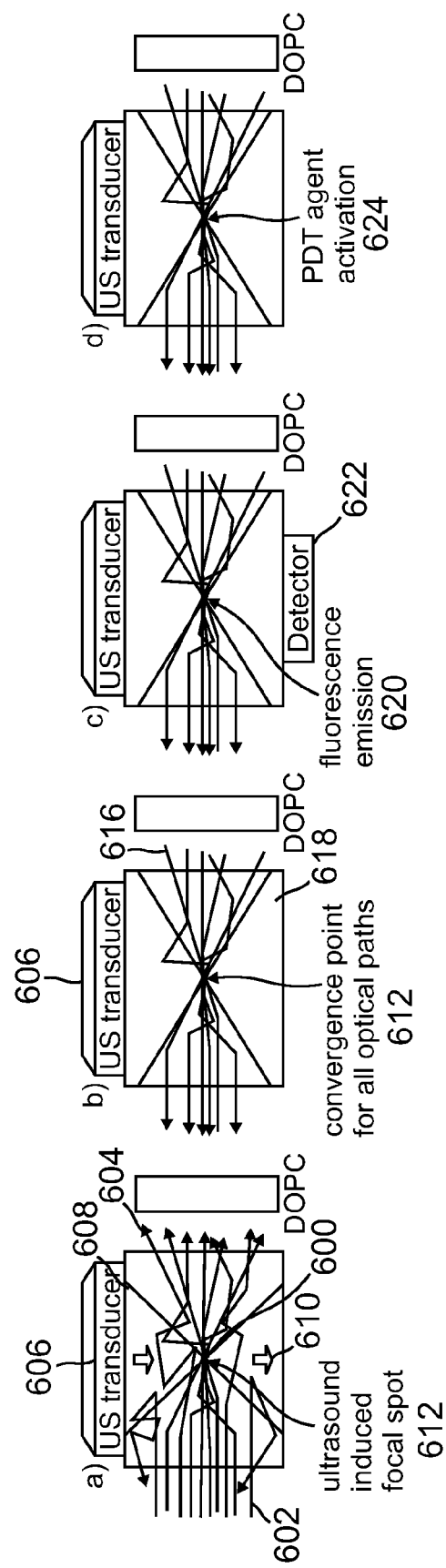
FIG. 6 are schematics for a TSOPC based optical focal spot generator, according to one or more embodiments of the present invention, wherein in FIG. 6(a) the present invention uses an ultrasound transducer (frequency=f) to focus acoustic power into a desired spatial point and arranges for the DOPC to lock onto and record the light field components (upshifted by f) that have passed through that focal point.

The ultrasound guided light focusing strategy described above can be applied in PDT procedures to provide the much needed ability to focus and steer light onto specific locations in tissues (see FIG. 6). The method may comprise the following steps.

Step 1, illustrated in FIG. 6(a), comprises illuminating the target 600 with a uniform light field 602 (shown entering the target from the left in FIG. 6(a)). Light diffuses through the target and some of that light 604 emerges from the right face of the target. Concurrent with this light 602 transmission, the step employs an ultrasound transducer 606 to generate a focused ultrasound beam 608 through the target 600 (ultrasound beam propagating in the direction of the arrows 610 in FIG. 6(a)). Unlike light, ultrasound is only weakly scattered by biological tissues. The technique of generating an ultrasound focus or ultrasound induced focal spot 612 within tissues is well-established and is the basis for ultrasound imaging. A fraction of the light 604 passing through this ultrasound focus may be shifted in frequency (the shift in frequency equals the ultrasound frequency).

Step 2, illustrated in FIG. 6(b), comprises selecting the frequency-shifted light field component of the light 604 for detection and measurement by a digital optical phase conjugation (DOPC) system. The DOPC system comprises an optical wavefront sensor that is capable of measuring the spatial phase and amplitude of an incoming light field of the light 604 interferometrically, and an SLM that is capable of altering a 'blank' light field into an OPC copy of the measured light field of the light 604. This step may comprise, by locking onto the frequency shift, using the DOPC system to accurately record the profile of the light field of the light 604 that has traveled through the ultrasound focus 612. Once the profile of the light field that has traveled through the ultrasound focus 612 is recorded, the step then further comprises turning off the ultrasound transducer 606 and the illumination light field, and using the DOPC system and a readout light field to generate an OPC light field 616. Since this is effectively a time-reversed copy of the light field of the beam 604 that has passed through the ultrasound focus 612, the OPC field 616 comes to a focus at the location of the ultrasound focus 612 which is the convergence point for all optical paths. This focused light field 616 can then be used to optically interrogate that targeted tissue region 600 with a resolution that is comparable to the ultrasound focus 612 resolution.

Step 3: Introducing a photosensitizing agent into tissue 618 of the human body or part/section thereof, so that the photosensitizing agent is also uptaken by the target (e.g., cancer cells) in the tissue or part of the human body.

Step 4: FIG. 6(c) illustrates how, in some embodiments, the next step may image the target 600 by making a fluorescence measurement, comprising measuring the total fluorescence emission 620 exiting the target 600. This measurement should correlate to the fluorophore concentration at the focus 612. To accomplish imaging, embodiments of the invention repeat a set of steps (the set comprising steps 1 and 2 illustrated in FIGS. 7(a) and 7(b), respectively), and altering the position of the ultrasound focus 612 through the target 600 between each set of steps. By making fluorescence measurement for each set, an image representative of the biochemical distribution map of the target 600 may be collected. The fluorescence is measured on a detector 622

However, instead of step 3 or in addition to step 3, the photodynamic therapy may further comprise using the time-reversed copy of the light field 616 that has passed through the ultrasound focus 612 to excite and activate the photosensitizing agent in the target 600 only (PDT target activation 624), thereby triggering biochemical reactions (e.g., apoptosis) at the location (at the focus 612) of the target 600 only.

Embodiments of the present invention may provide targeted PDT agent activation in tissue models, humans, and animal models. However, embodiments of the invention are not limited to these applications.

Note that the optical focusing method of the present invention may comprise steps 1, 2, and 4, as illustrated in FIGS. 6(a)-(c) or FIG. 1(a)-(c), as discussed in the first section.

Process Steps

Figure 7:
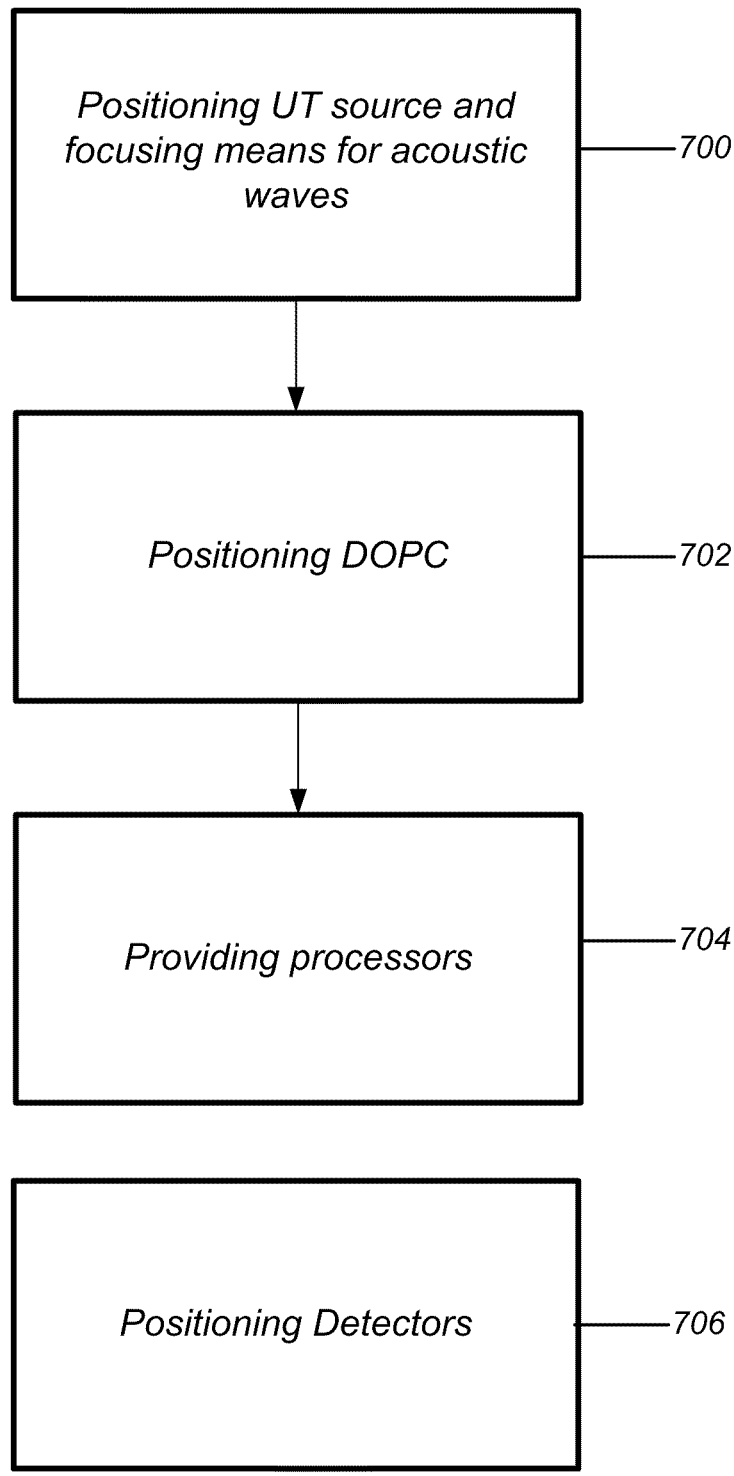
FIG. 7 is a flowchart illustrating a method of fabricating a microscope according to one or more embodiments of the present invention.

FIG. 7 illustrates a method of fabricating or assembling an imaging system (e.g., microscope) for imaging a sample (e.g., biological tissue) containing, e.g., one or more fluorescent agents. The method may comprise the following steps (and refers to elements of FIG. 2 and FIG. 6).

Block 700 represents positioning one or more sources (e.g. UT) of one or more signals 608, wherein the signals 608 propagate to one or more regions 612 of the sample 618. Input light 602, passing concurrently with the signals 608 through the regions 612, is modulated by the signals 608 into modulated light 604. One or more of the signals 608 may comprise one or more acoustic or ultrasound waves generated by one or more acoustic wave sources (such as ultrasound source UT). Thus, the sources may be for generating acoustic waves 608, and/or the system may include focusing means for the acoustic waves, so that the acoustic waves are focused at a focus 612 in the sample 618, wherein the acoustic waves modulate (e.g., frequency shift) light 602 passing through the focus 612. The signals (e.g., acoustic waves) may be focused to a single focus or focal spot 612, or multiple foci within the sample.

The acoustic waves 608 may modulate the input light by frequency shifting a frequency of the input light 602 by a single frequency f (where f is the frequency of the ultrasound or acoustic waves), or by a multiple of f (e.g., 2f, 3f). However, the present invention is not limited to modulation by frequency shifting.

The focus 612 of the ultrasound or acoustic waves 608 may have a diameter of 100 micrometers or less and/or be at a depth of at least 5 millimeters below a surface of the sample 618. The step may further comprise positioning a sample holder for holding the focus 612 within the sample 618. The holder may include a translation stage to translate the sample 618 such that the focus 612 moves controllably through the sample 618. Alternatively, the UT source can be scanned using a scanner.

Block 702 represents positioning a DOPC device. The DOPC may comprise a sensor (e.g., CCD) for detecting the modulated light inputted onto the sensor. The DOPC device may comprise at least one SLM to illuminate the sample 618 with an output beam or light 616 that is an optical phase conjugate of the modulated light or frequency shifted light beam 604, wherein the output beam or output light 616 is a reflection of a first reference light or blank beam 214 off one or more pixels of the SLM, and the pixels are for modulating the first reference light or blank beam 214 to create the optical phase conjugate in response to the modulated light detected by the sensor.

The DOPC device may include the SLM and the sensor for detecting the frequency shifted light beam inputted on the sensor, wherein the SLM is for outputting the output beam in response to the frequency shifted light beam detected by the sensor.

Thus, the step may further comprise positioning the SLM and the sensor (e.g., CCD) in the DOPC device, wherein the sensor is positioned for detecting the frequency shifted light beam 200 inputted on the sensor, and the SLM is for outputting the output beam 216, 616 in response to the frequency shifted light beam detected by the sensor.

The SLM may have a number of pixels greater than 512 by 512, for example, however the present invention is not limited by a particular number of pixels.

The DOPC may be selected to have an update rate of at least 70 Hz (e.g., by selecting an appropriate SLM and CCD), or faster than time scales of one or more movements in living tissues 618 that deteriorate the TSOPC reconstruction efficiency.

The step may include providing a source for the input light 602. The DOPC device may include the source of the input light (500 in FIG. 5), and the modulated light or frequency shifted light beam may be backscattered towards the DOPC device and collected by the sensor in the DOPC device.

However, the source of the input light 602 need not be included in the DOPC device. For example, the method may include positioning the source of the input light 602 and the SLM such that the input light 602 is transmitted through the sample 618 and the modulated light or frequency shifted light beam 604 is collected by the sensor in the DOPC device in a transillumination configuration. The method may comprise positioning a source of the input light 602 to illuminate the sample 618 so that at least part of the input light 602 passes through the focus 612 and interacts with the acoustic waves 608 at the focus 612, thereby generating, at the focus 612, the modulated light or frequency shifted light beam 604. The modulated light may be backscattered towards the DOPC device and collected by the DOPC device.

The step may further comprise positioning a source of the first reference light or blank beam 214, wherein the SLM outputs the output light or beam 616 that is a reflection of the first reference light or blank beam 214 directed onto the pixels of the SLM by a beamsplitter 202.

The step may further comprise positioning a beam splitter 202 to combine the modulated light or frequency shifted light beam 200, and a second reference light or beam 206, on the sensor (e.g., CCD) so that the modulated light or frequency shifted light beam 200 and the second reference beam 206 interfere on the sensor and form one or more holograms on the sensor, wherein the second reference beam 206 is modulated or frequency shifted by a frequency of the acoustic waves 608, so that the reference beam 206 only interacts interferometrically with the modulated frequency shifted light beam, and the holograms include interferometric data. The beamsplitter 202 may direct the modulated or frequency shifted light beam 200, and transmit the reference beam 206, for example.

The interferometric data that may be used to calculate the optical phase conjugate of the frequency shifted light beam that is outputted by the SLM.

The step may further comprise positioning an electro-optic modulator EO that controls a relative phase between the modulated or frequency shifted light beam 200 and the second reference beam 206, so that the holograms include one or more phase shifted holograms.

The first reference/blank beam 214 and the second reference beam 206 may be the same in some embodiments.

Block 704 represents providing and or connecting one or more processors 208 for receiving 210 the interferometric data and determining, from the interferometric data, one or more phases and one or more amplitudes of the modulated or frequency shifted light fields of the modulated light or frequency shifted light beams 200, digitally modifying (e.g., reversing) the phases and the amplitudes to produce modified phases and modified amplitudes, and outputting the modified (e.g., reversed) phases and modified (e.g., reversed) amplitudes to the SLM, so that the pixels reflect the output light or beam 216 having the output light fields with reversed phases and reversed amplitudes that are the optical phase conjugates of the phases and the amplitudes of the modulated or frequency shifted light beam.

The step may further comprise providing and/or connecting one or more computer processors for controlling the first reference light or beam's 214 output power such that an output power of the output light or beam 216, 616 is sufficient to excite the fluorescence 620 detected by the detector 622; synchronizing the acoustic waves 608 to the output light or beam 616 (e.g., using a function generator and signal amplifier); and controlling a power of the acoustic waves 608 to optimize efficiency of the modulation or frequency shifting of the modulated light or frequency shifted beam 604.

Block 706 represents positioning one or more detectors 622 to detect one or more resulting outputs that are based on an interaction between the output light 616 and the one or more regions 612 of the sample 618, thereby imaging the sample.

The output may comprise fluorescence generated by the output light exciting fluorescent agents in the one or more regions 612 (e.g., at the focal spot 612), thereby imaging the sample. The acoustic waves may be focused at a focus in the sample so that the one or more regions include a focal spot 612, and the detector 622 may be positioned to detect a threshold fraction of the fluorescence from the focal spot so that a fluorescence concentration at the focal spot is measured.

The input light 602 passing through the focus typically has a higher probability of absorbing a phonon generated by the acoustic waves as compared to the input light passing through the sample and outside the focus, so that increased fluorescence is detected from the focus as compared to from outside the focus.

A translation stage may be positioned for moving the focus with respect to the sample so that a plurality of foci and focal spots are produced within the sample, wherein the detector detects the resulting outputs at each of the foci, thereby mapping a fluorescence concentration distribution across the sample.

The output light may excite the fluorescence that is two-photon fluorescence. For example, the output light may comprise a longer wavelength, e.g., 1064 nm. At this longer wavelength, embodiments of the present invention may perform two photon fluorescence. A main advantage of embodiments that use the two photon implementation is that the background may be greatly suppressed, since the two photon effect preferentially (or, e.g., only) occurs at the focus of the output light outputted by the DOPC (e.g., at the focus defined by the acoustic waves). In one example, the output light from the DOPC, having a wavelength of 1064 nm, arrives at the focus or focal spot (defined by the acoustic waves) and excites the one or more fluorophores (or the one or more fluorescent agents) at a wavelength of 532 nm (due to the two photon effect).

In some embodiments, the fluorophores at the focus or focal spot are excitable at the two photon wavelength but not at the one photon wavelength at the focus. As a result, fluorophores that are not at the focus are typically not excited by the output light from the DOPC that is not at the focus (i.e., time-reversed light that is before or after the focus). Specifically, in the example where the wavelength of output light before and after the focus is 1064 nm, the output light does not excite fluorophores before and after the focus or outside the focus. As a result, only fluorophores at the focus are typically excited, decreasing the background. Specifically, in this example, some of the 1064 nm output light at the focus may, due to the 2 photon effect, become or generate fluorescence at 532 nm in wavelength (but only at the focus).

The acoustic waves may be focused at a focus in the sample so that the one or more regions include a focal spot, and the fluorescent agents may be photosensitizing agents that induce biochemical reactions only at the focal spot in response to excitation by the output beam only at the focus, thereby performing photodynamic therapy.

In other embodiments, the detector detects one or more of the following: an absorption, a scattering, or reflectance of the output light. For example, the imaging system may be used in optical coherence tomography to image the sample using the output light, or in confocal microscopy, or to perform Raman imaging.

FIG. 7 also illustrates a method of assembling an optical microscope for imaging a sample containing one or more fluorescent agents, comprising positioning a source for generating acoustic waves that are focused at a focus in the sample, wherein the acoustic waves frequency shift light passing through the focus; and at least one spatial light modulator (SLM) to illuminate the sample with an output beam that is an optical phase conjugate of the frequency shifted light beam, wherein the output beam is a reflection of a first reference beam off one or more pixels of the SLM, and the pixels are for modulating the first reference beam to create the optical phase conjugate, and a detector to detect fluorescence generated by the output beam exciting the fluorescent agents at the focus in the sample, thereby imaging the sample.

Figure 8:
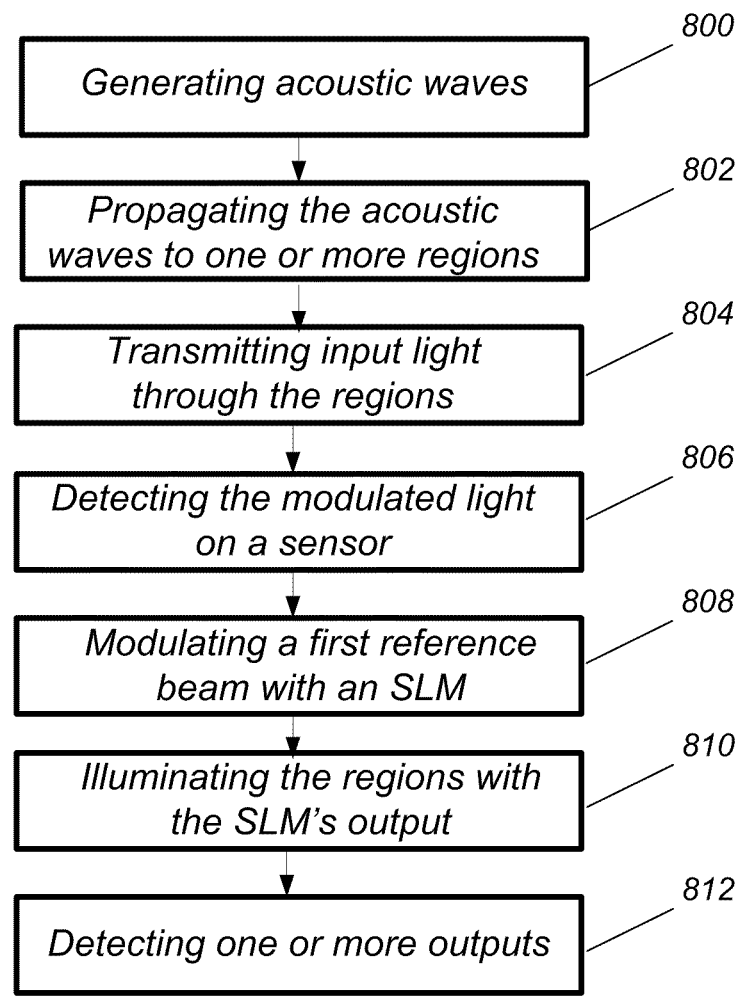
FIG. 8 is a flowchart illustrating a method of imaging a sample or performing photodynamic therapy according to one or more embodiments of the present invention.

FIG. 8 illustrates a method for imaging a sample using e.g., ultrasound or acoustic waves. The method may comprise the following steps.

Block 800 generating one or more signals from one or more sources (e.g., the acoustic waves from an acoustic wave source, e.g., ultrasound source UT).

Block 802 represents propagating, from one or more sources, one or more signals to one or more regions of the sample.

The step may further comprise focusing the signal (e.g., ultrasound or acoustic waves) at a single focus or multiple foci in the sample, so that the one or more regions include a single focal spot or multiple focal spots.

The focusing, e.g., using an objective, of the acoustic waves may be such that the focus of the acoustic waves has a diameter of 100 micrometers or less, and/or such that the focus is at a depth of at least 5 mm below a surface of the sample.

Block 804 represents transmitting input light through the one or more regions of the sample. The step may comprise modulating input light into modulated light, wherein the input light is modulated into the modulated light as the input light passes through the one or more regions of the sample concurrently with the signal.

The step may further comprise using the acoustic waves to modulate the input light by frequency shifting a frequency of the input light by a single frequency of the acoustic waves, or by multiples of the frequency of the acoustic waves.

The step may comprise transmitting the light through the sample and the focus such that the frequency shifted light beam is collected by the sensor in the DOPC device in a transillumination configuration.

The regions may comprise a focus or focal spot of the signal, wherein the signal (e.g., ultrasound or acoustic waves) modulate (e.g., frequency shift) input light passing through the focus into modulated (e.g., frequency shifted) light. The step may comprise illuminating, from a source included in the DOPC device, the sample such that at least part of the input light is transmitted through the sample, and the modulated light or frequency shifted light beam is backscattered towards the DOPC device and collected by the DOPC device.

Block 806 represents detecting, on the sensor, the modulated light or frequency shifted light. The modulated light may be collected by a sensor in a DOPC device in a transillumination configuration. The step may comprise directing, using a beam splitter, the modulated or frequency shifted light beam to the sensor; and transmitting, through the beam splitter, a sensor reference beam to the sensor so that the modulated light or frequency shifted light beam and the sensor reference beam interfere and produce interferometric data that is used to calculate or obtain the optical phase conjugate of the modulated light or frequency shifted light beam. The step may comprise combining, using a beamsplitter, the frequency shifted light beam and a second reference beam on the sensor, so that the frequency shifted light beam and the second reference beam interfere on the sensor and produce interferometric data that is used to calculate the optical phase conjugate of the frequency shifted light beam that is outputted by the SLM.

Block 808 represents using an SLM to output output light or an output light beam that is an optical phase conjugate of the modulated light or frequency shifted light beam, wherein the SLM outputs the output light or beam in response to the modulated light or frequency shifted light beam detected by the sensor, and the SLM and the sensor are included in a DOPC device. The step may comprise generating an SLM reference beam from a source; directing, using a beamsplitter, the SLM reference beam onto the pixels of the SLM, modulating the SLM reference beam using the SLM (e.g., by positioning the pixels of the SLM) to create the output beam or light, wherein the output beam or light is a reflection of a SLM reference beam off the one or more pixels of the SLM. If the sample is living tissue, the method may further comprise updating the DOPC device faster than one or more time scales of one or more movements in the living tissue that deteriorate a TSOPC reconstruction efficiency.

The method may comprise selecting a wavelength of the output light that excites the fluorescence that is two-photon fluorescence, thereby imaging the sample using two-photon fluorescence.

The method may further comprise providing one or more processors for receiving the interferometric data and determining input phases and the input amplitudes of input light fields of the input light 406 from the inteferometric data, digitally modifying (e.g., reversing the input phases and the input amplitudes to produce modified input phases and modified input amplitudes, and outputting the modified (e.g. reversed) input phases and modified (e.g., reversed) input amplitudes to the SLM 404 and so that the SLM 404 outputs the output light 410 having the modified input phases and modified input amplitudes that are the optical phase conjugates of the input phases and the input amplitudes.

The processors 208 may be connected to the sensor (e.g., CCD) to receive the amplitude and phase information of the modulated light or frequency shifted light beam, wherein the information is used for positioning the SLM pixels to create the optical phase conjugate of the input wave.

The present invention is not limited to the use of an SLM to produce the optical phase conjugate. Any device that may produce an optically phase conjugate the modulated or frequency shifted light may be used (e.g., a photorefractive crystal). For example, the optical phase conjugating device may digitally produce or create the optical phase conjugate of the frequency shifted light.

Block 810 represents allowing the output beam or light to retrace a path of the frequency shifted light beam, thereby illuminating the sample and exciting fluorescent agents in the sample in the regions or at the focus, for example. The step may further comprise controlling, using one or more processors, the SLM reference beam's output power such that an output power of the output light or beam is sufficient to excite the fluorescence detected by the detector; synchronizing, using the processors, the acoustic waves to the output beam or light; and controlling, using the processors, a power of the acoustic waves to optimize efficiency of the frequency shifting or modulation.

Block 812 represents detecting one or more resulting outputs that are based on an interaction between the output light and the one or more regions of the sample, thereby imaging the sample.

The step may comprise generating fluorescence by the output light exciting fluorescent agents in the one or more regions, thereby imaging the sample, wherein the outputs are the fluorescence.

The step may comprise positioning the detector to detect a threshold fraction of the fluorescence from the focal spot so that a fluorescence concentration at the focal spot is measured.

The method may further comprise moving the focus with respect to the sample and repeating steps of Blocks 800-812 so that a plurality of the foci are produced within the sample, wherein the detector detects the resulting outputs at each of the foci, thereby mapping a fluorescence concentration distribution across the sample.

The step may comprise using the excitation of the fluorescent agents. The step may comprise performing photodynamic therapy, wherein the fluorescent agents are photosensitizing agents that induce biochemical reactions (e.g., only) at the focus in response to excitation by the output beam only at the focus. The step may comprise detecting fluorescence generated by the output beam or light exciting the fluorescent agents at the focus in the sample, thereby imaging the sample.

The output light may have an output wavelength and an output frequency, and in one embodiment the fluorescent agents may comprise one or more materials that are only excited by a wavelength that is half of the output wavelength and twice the output frequency. The detectors may detect the fluorescence that is two-photon fluorescence resulting from two-photon excitation of the fluorescent agents (e.g., one or more fluorophores) at the focus by the output light. Resolution of the imaging device may be enhanced because fluorescence scales as the intensity squared of the output light, and therefore fluorescence from outside the focus is suppressed resulting in reduced detection of fluorescence from outside the focus by the detector.

The step may comprise using the imaging system to perform optical coherence tomography (OCT) to image the sample using the output light. One or more embodiments may use a conventional OCT system, but run it through the SLM to create the tissue transparency.

In other embodiments, the detector detects one or more of the following: an absorption, a scattering, or reflectance of the output light from the SLM, or as manifested in the output light from the SLM, and imaging of Raman scattering. Embodiments may use a separate probe beam at a different wavelength, but using the SLM output light as set by the DOPC. Then the amount of light that is scattered or reflected back from the target, through the SLM, may be measured.

In yet other embodiments, the imaging system includes a confocal microscope (including reflectance and fluorescence). In a reflective confocal microscope, there is only one objective, and a beamsplitter separates the transmitter and receiver paths. One or more embodiments may run the light through the SLM in both directions.

In yet other embodiments, the focus may be a single focus and two acoustic waves may be focused at the single focus to produce the modulated light, thereby improving 3-dimensional resolution of the imaging.

In yet other embodiments, the fluorescence may be used to measure aberrations or distortions to the input light caused by the sample, and the imaging system may correct for the aberrations or distortions, e.g., by re-positioning one or more optical elements in the imaging system so that light passing through a vicinity of the focus experiences reduced aberration or distortion, or by other methods.

Embodiments may function in the same way that astronomers image a small region around a guidestar. For direct imaging using the guidestar, one or more embodiments may also illuminate and view through the SLM. The ultrasound-generated guidestar may image a small region of tissue, moving the guidestar as needed to obtain a reasonable field of view.

The present invention is not limited to any particular light or light beams. The input light, the output light, the reference light, and the modulated light may comprise one or more input light beams, one or more output light beams, one or more reference light beams, and one or more frequency shifted or modulated light beams, respectively, for example. The frequency shifting is not limited to any particular kind of frequency shifting, and may include frequency shifting that does not result in a single frequency light wave.

Moreover, the present invention is not limited to any particular wavelengths. For example, the light 602, the frequency shifted light 200, the reference light, and the output light may have any wavelength, including optical wavelengths. Optical wavelengths may provide better resolution. The techniques may work over a large band of wavelengths, for example.

The present invention is not limited to the use of an SLM or digital optical phase conjugation. A photorefractive crystal may also be used to perform optical phase conjugation. Moreover, digital optical phase conjugation (e.g., digitally creating the optical phase conjugate) may be performed by other devices or methods.

Advantages and Improvements

Embodiments of the invention provide the ability to freely focus light deep within tissues at a depth and resolution that have never been accomplished in the optical regime. The availability of this proposed light focusing strategy is supported by the characterization of the time-reversal scattering suppression phenomenon [9] [10] [11] [12].

Embodiments of the present invention may open up new applications in biophotonics, biomedicine imaging, and therapeutics.

Embodiments of the invention demonstrate that tissue scattering need not obscure or prevent the ability to accomplish deep tissue high-resolution imaging. Embodiments of the invention may also overcome a number of potential issues and concerns associated with ultrasound based imaging.

In view of various embodiments described above, one consideration may be whether the proportion of light upmodulated by the ultrasound focus is sufficiently high. Such optical frequency upconversion is also used by ultrasound-modulation optical tomography [8]. However, embodiments of the invention utilize interferometric detection, which may provide more sensitive detection.

A further consideration is why one would not simply illuminate the tissue uniformly with excitation light, focus ultrasound at a point in the tissue and then detect the modulation in the fluorescence emission instead. However, such an approach has been tried previously [16]. By focusing the excitation light using the approach described above, embodiments of the present invention preferentially excite the relevant fluorophores and create a higher signal-to-noise. Furthermore, a light focus point in tissue may actually be generated. That high concentration of light at the focus can be used with Raman scattering or even absorption as the basis of image contrast.

An additional consideration relates to the selection of off-focal point light paths. Embodiments of the invention may shift the frequency of some light paths that pass through the off-focus volumes of the ultrasound beam with diminished efficiency. During the time-reversal playback, these light paths are also retraced but at a proportionately lower efficiency. This contributes to a low background and may have an impact on the sensitivity for deeper tissue penetration. This problem can be alleviated by using higher order photon-phonon interactions, such as higher order Raman-Nath interactions, to induce a sharper ultrasound-intensity associated photon frequency upconversion contrast during the signal measurement phase.

During the time-reversal playback, light travelling to and away from the optical focus may also excite surrounding fluorophores. As such, embodiments of the present invention expect a background during the fluorescence imaging process. This background may be much reduced if the fluorophores are highly localized. 2-photon fluorescence processes may be used to better enhance fluorescence from the focus spot to make better use of the intensity maximum associated with the focus spot.

Further, deeper imaging depth (e.g., 5 mm or greater) is possible than in the past. Also, initial imaging may be moderate in speed. The speed at which light can be focused at different points in the sample may be limited by the imaging rate of the sensors and the refresh rate of the spatial light modulator (SLM). At the specified rate of 70 Hz, one may render a 100×100 point fluorescence image in a time period of ~2 min. The TSOPC phenomenon is very robust versus wavefront noise [10], and, as such, a low bit depth but fast MEMS-mirror-based SLM can dramatically improve imaging speed at a modest image SNR cost.

REFERENCES

The following references are incorporated by reference herein.

1. Haka, A. S., K. E. Shafer-Peltier, M. Fitzmaurice, J. Crowe, R. R. Dasari, and M. S. Feld, *Diagnosing breast cancer by using Raman spectroscopy.* Proceedings of the National Academy of Sciences of the United States of America, 2005. 102(35): p. 12371-12376.

2. Denk, W., J. H. Strickler, and W. W. Webb, *2-PHOTON LASER SCANNING FLUORESCENCE MICROSCOPY.* Science, 1990. 248(4951): p. 73-76.

3. Wang, L. V., *Multiscale photoacoustic microscopy and computed tomography.* Nature Photonics, 2009. 3(9): p. 503-509.

4. Campagnola, P. J. and L. M. Loew, *Second-harmonic imaging microscopy for visualizing biomolecular arrays in cells, tissues and organisms.* Nat Biotech, 2003. 21(11): p. 1356-1360.

5. Vo-Dinh, T., *Biomedical photonics handbook.* 2003, New York: CRC press.

6. Huang, D., E. A. Swanson, C. P. Lin, J. S. Schuman, W. G. Stinson, W. Chang, M. R. Hee, T. Flotte, K. Gregory, C. A. Puliafito, and J. G. Fujimoto, *OPTICAL COHERENCE TOMOGRAPHY.* Science, 1991. 254(5035): p. 1178-1181.

7. Wang, L. V. and H.-i. Wu, *Biomedical optics: principles and imaging.* 2007, Hoboken, N.J.: Wiley-Interscience.

8. Wang, L. H. V., *Ultrasound-mediated biophotonic imaging: A review of acousto-optical tomography and photoacoustic tomography.* Disease Markers, 2003. 19(2-3): p. 123-138.

9. Yaqoob, Z., D. Psaltis, M. S. Feld, and C. Yang, *Optical phase conjugation for turbidity suppression in biological samples.* Nature Photonics, 2008. 2(2): p. 110-115.

10. Cui, M. and C. Yang, *Implementation of a digital optical phase conjugation system and its application to study the robustness of turbidity suppression by phase conjugation.* Optics Express, 2010. 18(4): p. 3444-3455.

11. Cui, M., E. J. McDowell, and C. Yang, *An in vivo study of turbidity suppression by optical phase conjugation (TSOPC) on rabbit ear.* Opt. Express, 2010. 18(1): p. 25-30.

12. McDowell, E. J., M. Cui, I. M. Vellekoop, V. Senekerimyan, Z. Yaqoob, and C. Yang, *Turbidity suppression from the ballistic to the diffusive regime in biological tissues using optical phase conjugation.* Journal of Biomedical Optics, 2010.

13. Leith, E. N. and J. Upatnieks, *Holographic imagery through diffusing media.* JOSA, 1966. 56: p. 523.

14. Hedlund, E. M., K. Hosaka, Z. D. Zhong, R. H. Cao, and Y. H. Cao, *Malignant cell-derived PIGF promotes normalization and remodeling of the tumor vasculature.* Proceedings of the National Academy of Sciences of the United States of America, 2009. 106(41): p. 17505-17510.

15. Griffin, R. J., B. W. Williams, J. C. Bischof, M. Olin, G. L. Johnson, and B. W. Lee, *Use of a fluorescently labeled poly-caspase inhibitor for in vivo detection of apoptosis related to vascular-targeting agent arsenic trioxide for cancer therapy.* Technology in Cancer Research & Treatment, 2007. 6(6): p. 651-654.

16. Yuan, B. and Y. Liu, *Ultrasound-modulated fluorescence from rhodamine B aqueous solution.* Journal Of Biomedical Optics, 2010. 15: p. 021321.

17 T. J. Dougherty, C. J. Gomer, B. W. Henderson, G. Joni, D. Kessel, M. Korbelik, J. Moan, and Q. Peng, "Photodynamic therapy," *Journal of the National Cancer Institute*, vol. 90, pp. 889-905, June 1998.

18. M. Wenner, "The most transparent research," Nat. Med. 15(10), 1106-1109 (2009).

19. L. V. Wang, "Multiscale photoacoustic microscopy and computed tomography," Nat. Photonics 3(9), 503-509 (2009).

20. I. M. Vellekoop, and A. P. Mosk, "Universal optimal transmission of light through disordered materials," Phys. Rev. Lett. 101(12), 120601 (2008).

21. Z. Yaqoob, D. Psaltis, M. S. Feld, and C. Yang, "Optical phase conjugation for turbidity suppression in biological samples," Nat. Photonics 2(2), 110-115 (2008).

22. I. M. Vellekoop, and A. P. Mosk, "Focusing coherent light through opaque strongly scattering media," Opt. Lett. 32(16), 2309-2311 (2007).

23. I. M. Vellekoop, E. G. van Putten, A. Lagendijk, and A. P. Mosk, "Demixing light paths inside disordered metamaterials," Opt. Express 16(1), 67-80 (2008).

24. M. Cui, E. J. McDowell, and C. H. Yang, "Observation of polarization-gate based reconstruction quality improvement during the process of turbidity suppression by optical phase conjugation," Appl. Phys. Lett. 95(12), 123702 (2009).

25. M. Cui, E. J. McDowell, and C. Yang, "An in vivo study of turbidity suppression by optical phase conjugation (tsopc) on rabbit ear," Opt. Express 18(1), 25-30 (2010).

26. A. Yariv, and P. Yeh, "Phase conjugate optics and real-time holography," IEEE J. Quantum Electron. 14(9), 650-660 (1978).

27. J. Feinberg, and R. W. Hellwarth, "Phase-conjugating mirror with continuous-wave gain," Opt. Lett. 5(12), 519-521 (1980).

28. R. C. Lind, and D. G. Steel, "Demonstration of the longitudinal modes and aberration correction properties of a continuous-wave dye laser with a phase-conjugate mirror," Opt. Lett. 6(11), 554-556 (1981).

29 I. Lindsay, "Specular reflection cancellation enhancement in the presence of a phase-conjugate mirror," J. Opt. Soc. Am. B 4(11), 1810-1815 (1987).

30. D. M. Pepper, "Observation of diminished specular reflectivity from phase-conjugate mirrors," Phys. Rev. Lett. 62(25), 2945-2948 (1989).

31. P. Yeh, Introduction to photorefractive nonlinear optics (John Wiley & Sons, Inc, New York, 1993).

32. D. P. M. Gower, Optical phase conjugation (Springer-Verlag, New York, 1994).

33. C. A. Primmerman, D. V. Murphy, D. A. Page, B. G. Zollars, and H. T. Barclay, "Compensation of atmospheric optical distortion using a synthetic beacon," Nature 353(6340), 141-143 (1991).

34. M. J. Booth, M. A. A. Neil, R. Juskaitis, and T. Wilson, "Adaptive aberration correction in a confocal microscope," Proc. Natl. Acad. Sci. U.S.A. 99(9), 5788-5792 (2002).

35. M. Rueckel, J. A. Mack-Bucher, and W. Denk, "Adaptive wavefront correction in two-photon microscopy using coherence-gated wavefront sensing," Proc. Natl. Acad. Sci. U.S.A. 103(46), 17137-17142 (2006).

36. D. Débarre, E. J. Botcherby, T. Watanabe, S. Srinivas, M. J. Booth, and T. Wilson, "Image-based adaptive optics for two-photon microscopy," Opt. Lett. 34(16), 2495-2497 (2009).

37. D. Débarre, E. J. Botcherby, M. J. Booth, and T. Wilson, "Adaptive optics for structured illumination microscopy," Opt. Express 16(13), 9290-9305 (2008).

38. Z. Yaqoob, D. Psaltis, M. S. Feld, and C. Yang, "Optical phase conjugation for turbidity suppression in biological samples " *Nature Photonics*, vol. 2, pp. 110 - 115, 2008.

39. M. Cui, E. McDowell, and C. Yang, "Observation of polarization-gate based reconstruction quality improvement during the process of turbidity suppression by optical phase conjugation," *Applied Physics Letters*, vol. 95, p. 123702, 2009.

40. E. N. Leith and J. Upatnieks, "Holographic imagery through diffusing media," *JOSA*, vol. 56, p. 523, 1966.

41. M. Wenner, "The most transparent research," *Nature Medicine*, vol. 15, p. 1106, 2009.

42. T. Vo-Dinh, *Biomedical Photonics Handbook.* Boca Raton, Fla.: CRC Press, 2003.

43. D. Huang, E. A. Swanson, C. P. Lin, J. S. Schuman, W. G. Stinson, W. Chang, M. R. Hee, T. Flotte, K. Gregory, C. A. Puliafito, and J. G. Fujimoto, "Optical Coherence Tomography," *Science*, vol. 254, pp. 1178-1181, Nov. 22 1991.

44. D. A. Boas, D. H. Brooks, E. L. Miller, C. A. DiMarzio, M. Kilmer, R. J. Gaudette, and Q. Zhang, "Imaging the body with diffuse optical tomography," *IEEE Signal Processing*, vol. 18, pp. 57-75, 2001.

45. E. Jakeman and K. D. Ridley, "Incomplete phase conjugation through a random phase screen. II. Numerical simulations," *JOSA A*, vol. 13, p. 2293, 1996.

46. S. C. W. Hyde, R. Jones, N. P. Barry, J. C. Dainty, P. M. W. French, K. M. Kwolek, D. D. Nolte, and M. R. Melloch, "Depth-resolved holography through turbid media using photorefraction," *IEEE JSTQE*, vol. 2, pp. 965-975, 1996.

47. I. Vellokoop and A. Mosk, "Universal Optimal Transmission of Light Through Disordered Materials," *Phys. Rev. Lett.*, vol. 101, p. 120601, 2008.

48. M. Fink, "Time-reversed acoustics," *Scientific American*, vol. 281, pp. 91-97, November 1999.

49. S. Hell and E. Stelzer, "Properties of a 4pi confocal fluorescence microscope," *JOSA A*, vol. 9, p. 2159, 1992.

50. L. Wang and X. Zhao, "Ultrasound-modulated optical tomography of absorbing objects buried in dense tissue-simulating turbid media," *Applied Optics*, vol. 36, p. 7277, 1997.

51. T. J. Dougherty, C. J. Gomer, B. W. Henderson, G. Joni, D. Kessel, M. Korbelik, J. Moan, and Q. Peng, "Photodynamic therapy," *Journal of the National Cancer Institute*, vol. 90, pp. 889-905, June 1998.

52. X. Cui, L. M. Lee, X. Heng, W. Zhong, P. W. Sternberg, D. Psaltis, and C. Yang, "Lensless high-resolution on-chip optofluidic microscopes for Caenorhabditis elegans and cell imaging," *PNAS*, vol. 105, p. 10670, 2008.

54. E. Check Hayden, "Microscopic marvels: Microscope for the masses," *Nature*, vol. 459, p. 632, 2009.

55. M. Fink, "Time reversed acoustics," Phys. Today 50(3), 34-40 (1997).

56. M. Fink, "Time-reversed acoustics," Sci. Am. 281(5), 91-97 (1999).

57. I. Yamaguchi, and T. Zhang, "Phase-shifting digital holography," Opt. Lett. 22(16), 1268-1270 (1997).

58. T. Zhang, and I. Yamaguchi, "Three-dimensional microscopy with phase-shifting digital holography," Opt. Lett. 23(15), 1221-1223 (1998).

59. A. Derode, A. Tourin, and M. Fink, "Random multiple scattering of ultrasound. Ii. Is time reversal a self-averaging process?" Phys. Rev. E Stat. Nonlin. Soft Matter Phys. 64(3), 036606 (2001).

60. J. W. Goodman, "Some fundamental properties of speckle," J. Opt. Soc. Am. 66(11), 1145-1150 (1976).

61. Meng Cui and Changhuei Yang, "Implementation of a digital optical phase conjugation system and its application to study the robustness of turbidity suppression by phase conjugation," Optics Express, Vol. 18, No. 4, published $2^{nd}$ February 2010.

62. Xiao Xu and Lihong V. Wang, "Time Reversal Ultrasound Modulated Optical Tomography Using A BSO Phase Conjugate Mirror", poster presentation, January 2009.

Conclusion

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. An imaging system for imaging a sample, comprising:
one or more sources of one or more signals, wherein the signals propagate to one or more regions of the sample and modulate input light into modulated light such that the input light is modulated into the modulated light as the input light passes through the one or more regions of the sample concurrently with the signals;
a Digital Optical Phase Conjugation (DOPC) device including:
a sensor for detecting the modulated light inputted onto the sensor, and
at least one spatial light modulator (SLM) positioned to illuminate the one or more regions with output light that is an optical phase conjugate of the modulated light, wherein the output light is a reflection of reference light from one or more pixels of the SLM, and the pixels modulate the reference light to create the output light in response to the modulated light detected by the sensor; and
one or more detectors positioned to detect one or more resulting outputs that are based on an interaction between the output light and the one or more regions of the sample, thereby imaging the sample.

2. The imaging system of claim 1, wherein one or more of the signals comprise one or more acoustic waves generated by one or more acoustic wave sources.

3. The imaging system of claim 2, wherein the output comprises fluorescence generated by the output light exciting fluorescent agents in the one or more regions, thereby imaging the sample.

4. The imaging system of claim 3, wherein:
the acoustic waves are focused at one or more focii in the sample so that the one or more regions include one or more focal spots, and
the detector is positioned to detect a threshold fraction of the fluorescence from the focal spots so that a fluorescence concentration at the focal spot is measured.

5. The imaging system of claim 4, further comprising a translation stage for moving the focus with respect to the sample so that a plurality of the foci and a plurality of the focal spots are produced within the sample, wherein the detector detects the resulting outputs at each of the foci, thereby mapping a fluorescence concentration distribution across the sample.

6. The imaging system of claim 3, wherein the output light excites the fluorescence that is two-photon fluorescence.

7. The imaging system of claim 3, further comprising:
a source of the reference light, wherein the SLM outputs the output light that is a reflection of the reference light directed onto the pixels of the SLM by a beamsplitter;
one or more computer processors for:
controlling the reference light's s output power such that an output power of the output light is sufficient to excite the fluorescence detected by the detector;
synchronizing the acoustic waves to the output light; and
controlling a power of the acoustic waves to optimize efficiency of the modulation of the input light by the acoustic waves.

8. The imaging system of claim 3, wherein:
the acoustic waves are focused at a focus in the sample so that the one or more regions include a focal spot, and
the fluorescent agents are photosensitizing agents that induce biochemical reactions only at the focal spot in response to excitation by the output beam only at the focus, thereby performing photodynamic therapy.

9. The imaging system of claim 2, wherein the acoustic waves modulate the input light by frequency shifting a frequency of the input light by a single frequency of the acoustic waves.

10. The imaging system of claim 2, wherein the imaging system is used in optical coherence tomography to image the sample using the output light.

11. The imaging system of claim 2, wherein:
the acoustic waves are focused at a focus in the sample so that the one or more regions include a focal spot, and
outputs are used to measure aberrations or distortions to the input light caused by the sample in the regions around the focus, and the imaging system corrects for the aberrations or distortions.

12. A method for imaging a sample, comprising:
(a) propagating, from one or more sources, one or more signals to one or more regions of the sample;
(b) modulating input light into modulated light, wherein the input light is modulated into the modulated light as the input light passes through the one or more regions of the sample concurrently with the signals;
(c) detecting, on a sensor, the modulated light inputted onto the sensor,
illuminating the one or more regions with output light outputted from at least one spatial light modulator (SLM), wherein the output light is an optical phase conjugate of the modulated light, the output light is a reflection of reference light from one or more pixels of the SLM, and the pixels modulate the reference light to create the output light in response to the modulated light detected by the sensor; and
(d) detecting one or more resulting outputs that are based on an interaction between the output light and the one or more regions of the sample, thereby imaging the sample.

13. The method of claim 12, wherein one or more of the signals comprise one or more acoustic waves generated by one or more acoustic wave sources.

14. The method of claim 13, further comprising generating fluorescence by the output light exciting fluorescent agents in the one or more regions, thereby imaging the sample, wherein the outputs are the fluorescence.

15. The method of claim 14, further comprising:
focusing the acoustic waves at one or more focii in the sample so that the one or more regions include one or more focal spots, and
positioning the detector to detect a threshold fraction of the fluorescence from the focal spots so that a fluorescence concentration at the focal spot is measured.

16. The method of claim 15, further comprising:
(e) moving the focus with respect to the sample and repeating steps (a)-(d) so that a plurality of the foci are produced within the sample, wherein the detector detects the resulting outputs at each of the foci, thereby mapping a fluorescence concentration distribution across the sample.

17. The method of claim 14, further comprising selecting a wavelength of the output light that excites the fluorescence that is two-photon fluorescence, thereby imaging the sample using two-photon fluorescence.

18. The method of claim 14, further comprising:
directing, from a source of the reference light, the reference light onto the pixels of the SLM so that the SLM outputs the output light that is a reflection of the reference light from the pixels of the SLM;
controlling the reference light's s output power such that an output power of the output light is sufficient to excite the fluorescence detected by the detector;
synchronizing the acoustic waves to the output light; and
controlling a power of the acoustic waves to optimize efficiency of the modulation of the input light by the acoustic waves.

19. The imaging system of claim 14, further comprising:
focusing the acoustic waves at a focus in the sample so that the one or more regions include a focal spot; and
performing photodynamic therapy by using the fluorescent agents as photosensitizing agents that induce biochemical reactions only at the focal spot in response to excitation by the output beam only at the focus.

20. The method of claim 13, further comprising using the acoustic waves to modulate the input light by frequency shifting a frequency of the input light by a single frequency of the acoustic waves.

21. The method of claim 13, further comprising using the imaging system to perform optical coherence tomography to image the sample using the output light.

22. The method of claim 13, wherein the acoustic waves are focused at a focus in the sample so that the one or more regions include a focal spot, and the method further comprises:
using the outputs to measure aberrations or distortions to the input light caused by the sample in the regions around the focus, and
correcting for the aberrations or the distortions.

23. The method of claim 13, further comprising:
focusing the acoustic waves at a focus in the sample so that there is a single region including a single focal spot.

* * * * *

UNITED STATES PATENT AND TRADEMARK OFFICE
CERTIFICATE OF CORRECTION

PATENT NO. : 8,450,674 B2  
APPLICATION NO. : 12/943841  
DATED : May 28, 2013  
INVENTOR(S) : Yang et al.

Page 1 of 1

It is certified that error appears in the above-identified patent and that said Letters Patent is hereby corrected as shown below:

Title Page, Item (75), should read,

Changhuei Yang, Pasadena, CA (US);
Charles DiMarzio, Cambridge, MA (US); Meng Cui, Ashburn, VA (US);
Ying Min Wang, Pasadena, CA (US);
Benjamin Judkewitz, Los Angeles, CA (US)

Signed and Sealed this
Second Day of July, 2013

Teresa Stanek Rea
*Acting Director of the United States Patent and Trademark Office*